United States Patent
Olender et al.

(10) Patent No.: US 12,315,149 B2
(45) Date of Patent: May 27, 2025

(54) SYSTEMS AND METHODS FOR UTILIZING SYNTHETIC MEDICAL IMAGES GENERATED USING A NEURAL NETWORK

(71) Applicant: MASSACHUSETTS INSTITUTE OF TECHNOLOGY, Cambridge, MA (US)

(72) Inventors: Max Louis Olender, Cambridge, MA (US); Elazer R. Edelman, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 375 days.

(21) Appl. No.: 17/793,201

(22) PCT Filed: Jan. 19, 2021

(86) PCT No.: PCT/US2021/013929
§ 371 (c)(1),
(2) Date: Jul. 15, 2022

(87) PCT Pub. No.: WO2021/146699
PCT Pub. Date: Jul. 22, 2021

(65) Prior Publication Data
US 2023/0076868 A1    Mar. 9, 2023

Related U.S. Application Data

(60) Provisional application No. 62/962,641, filed on Jan. 17, 2020.

(51) Int. Cl.
*G06T 7/00* (2017.01)
*G06N 3/045* (2023.01)
(Continued)

(52) U.S. Cl.
CPC .......... *G06T 7/0012* (2013.01); *G06N 3/045* (2023.01); *G06T 5/77* (2024.01); *G16H 30/40* (2018.01);
(Continued)

(58) Field of Classification Search
None
See application file for complete search history.

(56) References Cited

U.S. PATENT DOCUMENTS 11,625,812 B2 *   4/2023   Chandra .............. G06V 10/774
                                                      382/157
2007/0052700 A1   3/2007   Wheeler et al.
(Continued)

OTHER PUBLICATIONS

International Search Report of International Application No. PCT/US2021/013929 mailed May 24, 2021, 4 pages.
(Continued)

*Primary Examiner* — Leon Flores
(74) *Attorney, Agent, or Firm* — Quarles & Brady, LLP

(57) ABSTRACT

A system for completing a medical image having at least one obscured region includes an input for receiving a first classification map generated using an acquired optical coherence tomography (OCT) image having at least one obscured region, the acquired OCT image acquired using an imaging system and a pre-processing module coupled to the input and configured to create an obscured region mask. The pre-processing module also generates a second classification map that has the at least one obscured region filled in. The system also includes a generative network coupled to the pre-processing module and configured to generate a synthetic OCT image based on the second classification map and a post-processing module coupled to the generative network. The post-processing module is configured to receive the synthetic OCT image and the acquired OCT
(Continued)

image and to generate a completed image based on the synthetic OCT image and the acquired OCT image.

16 Claims, 16 Drawing Sheets

(51) Int. Cl.
    *G06T 5/77*     (2024.01)
    *G16H 30/40*     (2018.01)

(52) U.S. Cl.
    CPC ............... *G06T 2207/10101* (2013.01); *G06T 2207/10132* (2013.01); *G06T 2207/20081* (2013.01); *G06T 2207/20084* (2013.01); *G06T 2207/20221* (2013.01)

(56) References Cited

U.S. PATENT DOCUMENTS

| | | |
|---|---|---|
| 2008/0226123 A1 | 9/2008 | Birtwistle et al. |
| 2011/0310110 A1 | 12/2011 | Lookingbill et al. |
| 2014/0300864 A1 | 10/2014 | Fukuma et al. |
| 2015/0213629 A1 | 7/2015 | Celi et al. |
| 2019/0053750 A1 | 2/2019 | Chandrakasan et al. |
| 2020/0286208 A1* | 9/2020 | Halupka ................. G06N 3/045 |
| 2022/0245769 A1* | 8/2022 | Galeotti ................... G06N 3/08 |

OTHER PUBLICATIONS

Written Opinion of International Application No. PCT/US2021/013929 mailed May 24, 2021, 6 pages.

P. Isola et al., "Image-to-Image Translation with Conditional Adversarial Networks," in 2017 IEEE Conference on Computer Vision and Pattern Recognition (CVPR), 2017, vol. 2017—Janua, pp. 5967-5976.

Armanious et al., "MedGAN: Medical Image Translation using GANs," arXiv:1806.06397v2 [cs.CV] 2019.

Athanasiou et al. "Methodology for fully automated segmentation and plaque characterization in intracoronary optical coherence tomography images," Journal of Biomedical Optics 19 (2), Feb. 2014.

Dar et al. "Synergistic Reconstruction and Synthesis via Generative Adversarial Networks for Accelerated Multi-Contrast MRI," arXiv:1805.10704v1 [cs.CV] 2018.

Olender et al., "A mechanical Approach for Smooth Surface Fitting to Delineate Vessel Walls in Optical Coherence Tomography Images," IEEE Transactions on Medical Imaging, Nov. 2018.

Ronneberger et al., "U-Net: Convolutional Networks for Biomedical Image Segmentation," arXiv:1505.04597v1 [cs.CV] 2015.

Stimpel et al., "Projection image-to-image translation in hybrid x-ray/MR imaging," Proc. SPIE 10949, Medical Imaging 2019: Image Processing, 109492K (Mar. 15, 2019).

Sun et al., "An Adversarial Learning Approach to Medical Image Synthesis for Lesion Removal," arXiv:1810.10850v1 [cs.CV] 2018.

Yang et al., "Predicting CT Image from MRI Data through Feature Matching with Learned Nonlinear Local Descriptors," IEEE Transactions on Medical Imaging, Dec. 2017.

Yi et al., "Generative Adversarial Network in Medical Imaging: A Review," arXiv:1809.07294v3 [cs.CV] 2019.

* cited by examiner

SYSTEMS AND METHODS FOR UTILIZING SYNTHETIC MEDICAL IMAGES GENERATED USING A NEURAL NETWORK

CROSS-REFERENCE TO RELATED APPLICATIONS

This application is a 371 application of PCT/US2021/013929 filed Jan. 19, 2021, which based on, claims priority to, and incorporates herein by reference in its entirety U.S. Ser. No. 62/962,641 filed Jan. 17, 2020, and entitled "Systems and Methods For Utilizing Synthetic Medical Images Using A Neural Network."

BACKGROUND

Optical coherence tomography (OCT) is an imaging modality that utilizes light to perform imaging which allows resolutions (10-20 µm axially, 20-40 µm laterally) that result in highly detailed imaging at the near field. OCT has a much higher resolution than other intravascular imaging modalities. OCT may be used to image coronary vessels to, for example, diagnose and treat coronary artery disease (CAD). Intravascular OCT is catheter-based and produces high-resolution tomographic images of arterial lumens and vessel wall morphology using interferometry. OCT calculates the proportion of the light backscattered and absorbed by the vessel tissue and reconstructs two-dimensional (2D) images which represent the cross-sections (e.g., tomographic information) of the imaged vessel. Similar to other intravascular imaging modalities, such as intravascular ultrasound IIVUS), OCT can provide accurate measurements of a vessel, assess wall morphology, and allow detection of several different tissue types which are generally classified as calcified, lipid, fibrous, or mixed tissue. Moreover, use of OCT enables the detection of features that are associated with plaque vulnerability, including the measurement of fibrous cap thickness which cannot be accurately evaluated by other intravascular imaging techniques (e.g., IVUS). OCT has become popular for use in interventional cardiology. For example, the superiority of OCT in detecting features that are associated with plaque vulnerability, including the measurement of fibrous cap thickness, has made it a method of choice in clinical cardiology.

Analysis of a diseased arterial wall may be performed manually or automatically using machine learning methods to detect and classify mural (vessel wall) composition of atherosclerotic vessels. Machine learning methods, such as deep leaning, may also be used to generate synthetic medical images for various imaging modalities including OCT. Previous methods for generating OCT images have only been able to generate images of exceptionally simple physical systems (e.g., gelatinous cubes with a hard inclusion).

It would be desirable to provide systems and methods that utilize synthetic medical images (e.g., OCT images) of complex physical systems (e.g., arterial walls) generated by a neural network to, for example, perform image processing and analysis applications.

SUMMARY OF THE DISCLOSURE

In accordance with an embodiment, a system for completing a medical image having at least one obscured region includes an input for receiving a first classification map generated using an acquired optical coherence tomography (OCT) image having at least one obscured region, the acquired image acquired using an imaging system, a pre-processing module coupled to the input and configured to create an obscured region mask and to generate a second classification map that has the at least one obscured region filled in, a generative network coupled to the pre-processing module and configured to generate a synthetic OCT image based on the second classification map, and a post-processing module coupled to the generative network and configured to receive the synthetic OCT image and the acquired OCT image and to generate a completed image based on the synthetic OCT image and the acquired OCT image.

In accordance with another embodiment, a method for completing a medical image having at least one obscured region includes receiving a first classification map generated using an acquired optical coherence tomography (OCT) image having at least one obscured region, the acquired OCT image acquired using an imaging system, creating an obscured region mask, generating a second classification map that has the at least one obscured region filled in, generating a synthetic OCT image based on the second classification map using a generative network, generating a completed image based on the synthetic OCT image and the acquired OCT image, and displaying the completed image on a display or storing the completed image in a memory.

In accordance with another embodiment, a system for identifying at least one characteristic in an acquired medical image incudes an input for receiving a classification map generated using an acquired intravascular image acquired using an imaging system, a generative network coupled to the input and configured to generate a synthetic intravascular image based on the classification map, and a post processing module coupled to the generative network and configured to receive the synthetic intravascular image and the acquired intravascular image and to compare the synthetic intravascular image and the acquired intravascular image to generate a set of comparison results.

In accordance with another embodiment, a method for identifying at least one characteristic in an acquired medical image includes receiving a classification map generated using an acquired intravascular image acquired using an imaging system, generating a synthetic intravascular image based on the classification map using a generative network, comparing the synthetic intravascular image and the acquired intravascular image using a post-processing module to generate a set of comparison results, and displaying the comparison results on a display or storing the comparison results in a memory.

In accordance with another embodiment, a method for determining a parameter or material property associated with a procedure includes providing a plurality of perturbed model systems, each perturbed model system having an associated classification map and generating a plurality of synthetic images using a generative network. The plurality of synthetic images include at least one synthetic image associated with each of the plurality of perturbed model systems and each synthetic image is generated based on the classification map associated with one of the plurality of perturbed model systems. The method also includes receiving a procedure image acquired during or after the procedure is performed on a region of interest of a subject, comparing the plurality of synthetic images and procedure image using a post-processing module to determine at least one parameter or material property associated with the procedure, and displaying the at least one parameter or material property on a display or storing the at least one parameter or material property in a memory.

In accordance with another embodiment, a system for merging two or more medical images of a subject acquired using two or more imaging modalities includes an input for receiving a first classification map generated using a first intravascular image acquired using an imaging system associated with a first imaging modality and for receiving a second classification map generated using a second intravascular image acquired using an imaging system associated with a second imaging modality and a pre-processing module coupled to the input and configured to create a merged classification map based on the first classification map and the second classification map. The merged classification map includes information from at least one of the first classification map and the second classification map. The system further includes a generative network coupled to the pre-processing module. The generative network is configured to generate a synthetic merged image based on the merged classification map.

In accordance with another embodiment, a method for merging two or more medical images of a subject acquired using two or more imaging modalities includes receiving a first classification map generated using a first intravascular image acquired using an imaging system associated with a first imaging modality, receiving a second classification map generated using a second intravascular image acquired using an imaging system associated with a second imaging modality, and generating a merged classification map based on the first classification map and the second classification map. The merged classification map includes information from at least one of the first classification map and the second classification map. The method further includes generating a synthetic merged image based on the merged classification map using a generative network and displaying the synthetic merged image on a display or storing the synthetic merged image in a memory.

BRIEF DESCRIPTION OF THE DRAWINGS

The present invention will hereafter be described with reference to the accompanying drawings, wherein like reference numerals denote like elements.

DETAILED DESCRIPTION

The present disclosure describes various systems and methods for utilizing medical images generated using a neural network. The neural network may be used to generate synthetic medical images of tissues or systems which may or may not have a basis in a physical, existing tissue or system. In an embodiment, a generative network may be trained to generate an optical coherence tomography (OCT) image based on a classification map. While the following description of FIGS. 1-12 is discussed in terms of generating OCT images, it should be understood that the systems and methods described herein may be used to generate other types of medical images, e.g., IVUS, CT, MR, X-ray, ultrasound, etc. As used herein, the term "image" will be used to refer to any digital spatial representation of a physical system, including the distribution or intensity of reflected waves (e.g., optical, ultrasound, radiofrequency, etc.) and discrete representations of functional response or maps of properties (e.g., elastogram). In addition, as used herein, the term "imaging system" will be used to refer to any system which may be used in the acquisition of data or signals from a patient and the generation of an "image" (as defined above).

Figure 1:
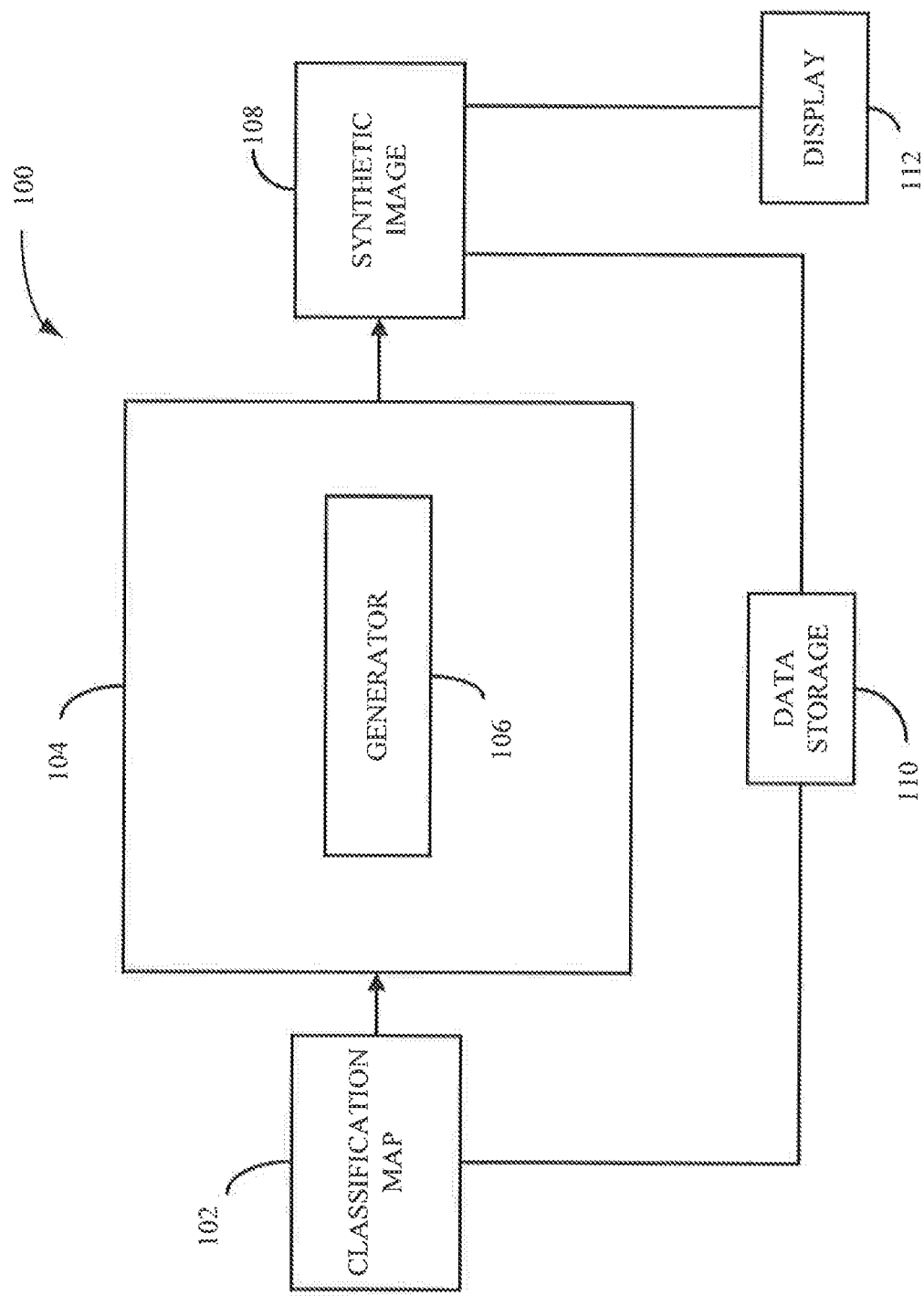
FIG. 1 is a block diagram of a system for generating a medical image using a generative network in accordance with an embodiment.

FIG. 1 is a block diagram of a system for generating a medical image using a generative network in accordance with an embodiment. System 100 includes a trained generative network 104 that includes a generator 106. A classification map 102 may be input to the generative network 104. The classification map may be retrieved, for example, from data storage (or memory) 110 of an imaging system (e.g., an OCT system) or other computer system. In various embodiments, classification map 102 may be entirely contrived, determined through characterization of an OCT image, determined through characterization of images from alternative imaging modalities, extracted directly by tissue characterization methods (e.g., virtual histology IVUS), defined by a computational model, or estimated from other data sources. The classification map may be generated using known methods. An example method for generating a classification map is described further below with respect to FIG. 3. In one embodiment, the classification map is a characterized OCT image of a coronary artery cross-section. For example, classification map 102 may subdivide an arterial wall into one of six different classes: calcium, lipid tissue, fibrous tissue, mixed tissue, non-pathological tissue or media, and no visible tissue.

Generative network 104 is configured to construct a realistic synthetic image 108 (e.g., an OCT image, or other type of medical image) based on the input classification map 102. The synthetic image may be, for example, a full or partial image. The classification map 102 may be input to the trained generator 106 which then generates a synthetic image 108 (e.g., an OCT image) based on the classification map 102. System 100 is configured to perform a form of image-to-image translation (prediction of pixels from pixels), for example, translating labels (e.g., the classification map) into a full image. The generative network 104 may be implemented using known models or network architectures such as, for example, U-Net. In one embodiment, the architecture of the generative network 104 may be modified to include additional paired layers, namely, one downsampling layer and one upsampling layer to accommodate larger input images (e.g., a classification map). The generated synthetic image 108 may be stored in data storage (or memory) 110 of an imaging system (e.g., an OCT system) or other computer system. The generated OCT image 108 (or other type of generated medical image) may also be provided to and displayed on a display 112.

Known methods may be used to train the generative network 104. The generative network 104 may be trained using a set of training data including classification maps (or characterized images) and the associated medical images (e.g., OCT images) used to generate the classification maps. In one embodiment, the classification maps 102 are characterized images of coronary artery cross-sections (that include representation of various classified tissue types comprising a wall of the artery) and the associated medical images are intravascular OCT images or intravascular images from other intravascular imaging modalities, for example, IVUS, etc. As mentioned above, the classification maps may be generated using known methods. The maps may be formatted in standard data structures such as a two-dimensional (2D) class numeric label map, three-dimensional (3D) color-coded images, or multi-dimensional one-hot encodings. The associated images may be 2D greyscale or intensity images or 3D images (e.g., 3D color images).

Figure 2:
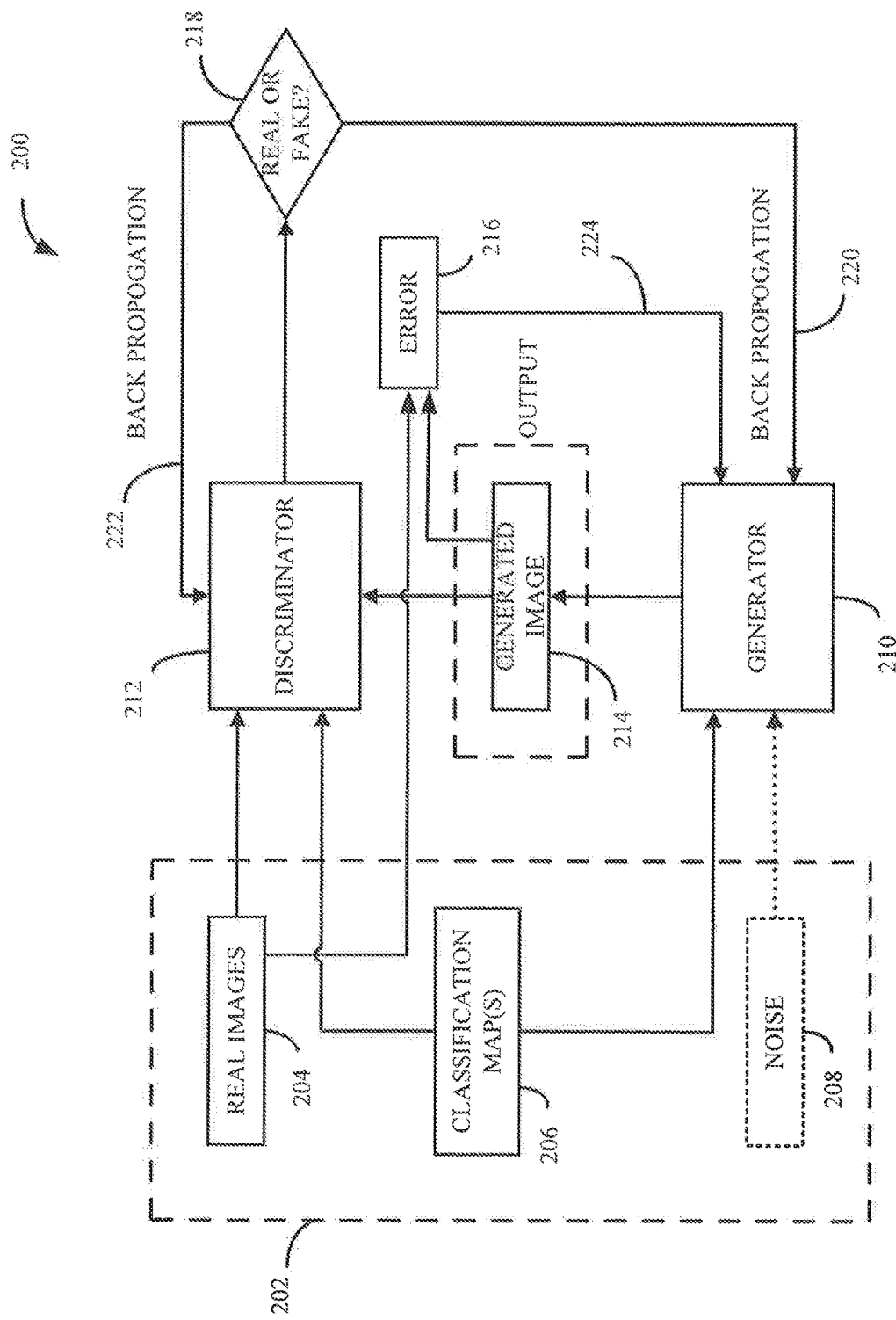
FIG. 2 is a block diagram of a conditional generative adversarial network for training a generative network and a discriminative network in accordance with an embodiment.

In one embodiment, the generative network 104 is trained using a conditional generative adversarial network (cGAN). FIG. 2 is a block diagram of a conditional generative adversarial network for training a generative network and a discriminative network in accordance with an embodiment. cGAN 200 includes a generative network (or generator) 210 and a discriminative network (or discriminator) 212. Generator 210 and discriminator 212 are configured to receive input data and images 202. Generator 210 receives input data including classification maps 206. In an embodiment, generator 210 may also receive noise 208. Noise 208 may be random noise generated from, for example, a normal distribution. Classification maps 206 may be retrieved, for example, from data storage (e.g., data storage 110 shown in FIG. 1) of an imaging system (e.g., an OCT system) or other computer system. In one embodiment, the classification maps 206 are characterized OCT images of coronary artery cross-sections. For example, classification maps 206 may subdivide an arterial wall into one of six different classes: calcium, lipid tissue, fibrous tissue, mixed tissue, non-pathological tissue or media, and no visible tissue. Discriminator 212 receives input data and images from input 202 including real (or training) images 204 and the classification maps 206 associated with the real images. In an embodiment, the classification maps 206 provided to the generator 210 and the discriminator 212 may be the same classification maps. In another embodiment, different classification maps may be used as input for each of the generator 210 and the discriminator 212. The real images may be 2D or 3D images. In one example, single images may be provided as input. In other examples, several tomographic images may be provided simultaneously as input or voxelized data may be provide as input. In one embodiment, the real (or training) images 204 are intravascular OCT images acquired by an OCT system. Real images 204 may be retrieved, for example, from data storage (e.g., data storage 110 shown in FIG. 1) of an imaging system (e.g., an OCT system) or other computer system. In an embodiment, the real images 204 may be retrieved from, for example, a picture archiving and communication system and may be, for example, DICOM (digital imaging and communication in medicine) images.

In another embodiment, parameters of the cGAN 200, such as $\lambda$ (lambda), which represents the relative weight attributed to GAN discrimination ($\mathcal{L}_{cGAN}(G, D)$) relative to the L1 distance ($\mathcal{L}_{L1}(G)$) in calculating generator loss, and the number of training epochs (cycles through the full training dataset) may be modified. In one embodiment, randomness may be induced in the training dataset including real images 204. For OCT images, the center of the image, which always incudes a predictable imaging artifact, should generally remain fixed due to the polar nature of the image's acquisition. Accordingly, applying random jittering and mirroring to the training dataset, which are common practices to reduce overfitting during network training, may not be productive. However, the image orientation around that center point in the OCT images (e.g., real images 204) is arbitrary, so random rotation may instead be implemented to introduce randomness to the training dataset. In an embodiment, random mirroring may be retained in the training dataset. In another embodiment of the cGAN 200, the adversarial aspect of the network may not be strictly necessary because loss functions directly penalizing deviation between generated and real images (e.g., L1 distance) may be sufficient to train a generator to produce relatively convincing, though sometimes somewhat blurry images.

Generator 210 is configured to generate images that mimic the real (or training) images 204 using the classification maps 206. In another embodiment, generator 210 may optionally also use noise 208 to generate an image that mimics a real image. Each generated image 214 is provided as an output from the generator 210. Each generated image 214 is also input to the discriminator 212. As mentioned above, the real images 204 and classification maps 206 are also input to the discriminator 212. The discriminator 212 is configured to distinguish the generated image 214 from the real images 204. Namely, the discriminator 212 evaluates the generated image 214 for authenticity, i.e., the discriminator 212 determines whether each image it receives from the generator 210 belongs to the real image 204 set.

During training, the discriminator 212 takes as input one or more samples from the real images 204, the classification maps 206 and the generated image 214 and determines whether the generated image 214 is real or fake at block 218. In addition, the discriminator 212 also determines whether a particular real image 204 received from the input 202 is real or fake 218. An error module 216 receives a real image 204 and the generated image 214 and compares the real image 204 to the generated image 214 to calculate an error 216 (e.g., the loss resulting from the differences between the generated 214 and real 204 images). The determination of whether a particular image 214 generated by generator 210 is real or fake 218 and the determination whether a particular real image 204 is real or fake is provided back to the discriminator 212 via back propagation 222. In this manner, the discriminator 212 may be penalized either for classifying the generated image 214 as real or for classifying the real image as fake. The determination of whether a particular image 214 generated by generator 210 is real or fake 218 is provided back to the generator 210 via back propagation 220. The calculated error 216 is also provided by back propagation 224 back to the generator 210. In one embodiment, the generative network 210 and the discriminative network 212 play a continuous game where the generator 210 is learning to provide more and more realistic images and the discriminator 212 is learning to get better at distinguishing generated image 214 from real images 204. In one example, the training of the cGAN 200 may continue until the generator 210 substantially reproduces the real images 204 and the discriminator 212 is guessing at random, unable to find a difference between the generate image 214 and the real images 204. cGAN 200, once trained, can be used to simulate images that are similar or indistinguishable from the real images. In another embodiment, the discriminator 212 may be trained (either fully or in part) prior to the training of the generator 210 (e.g., by using noise rather than generated images). As discussed above with respect to FIG. 1, the trained generator 210 (or generator 106 shown in FIG. 1) may be used to generate an OCT image 108 based on a classification map 102. In addition, the trained discriminator may be used for various applications as discussed further below, for example, to quantify a confidence in a classification method based on the classification map and its associated image.

Figure 3:
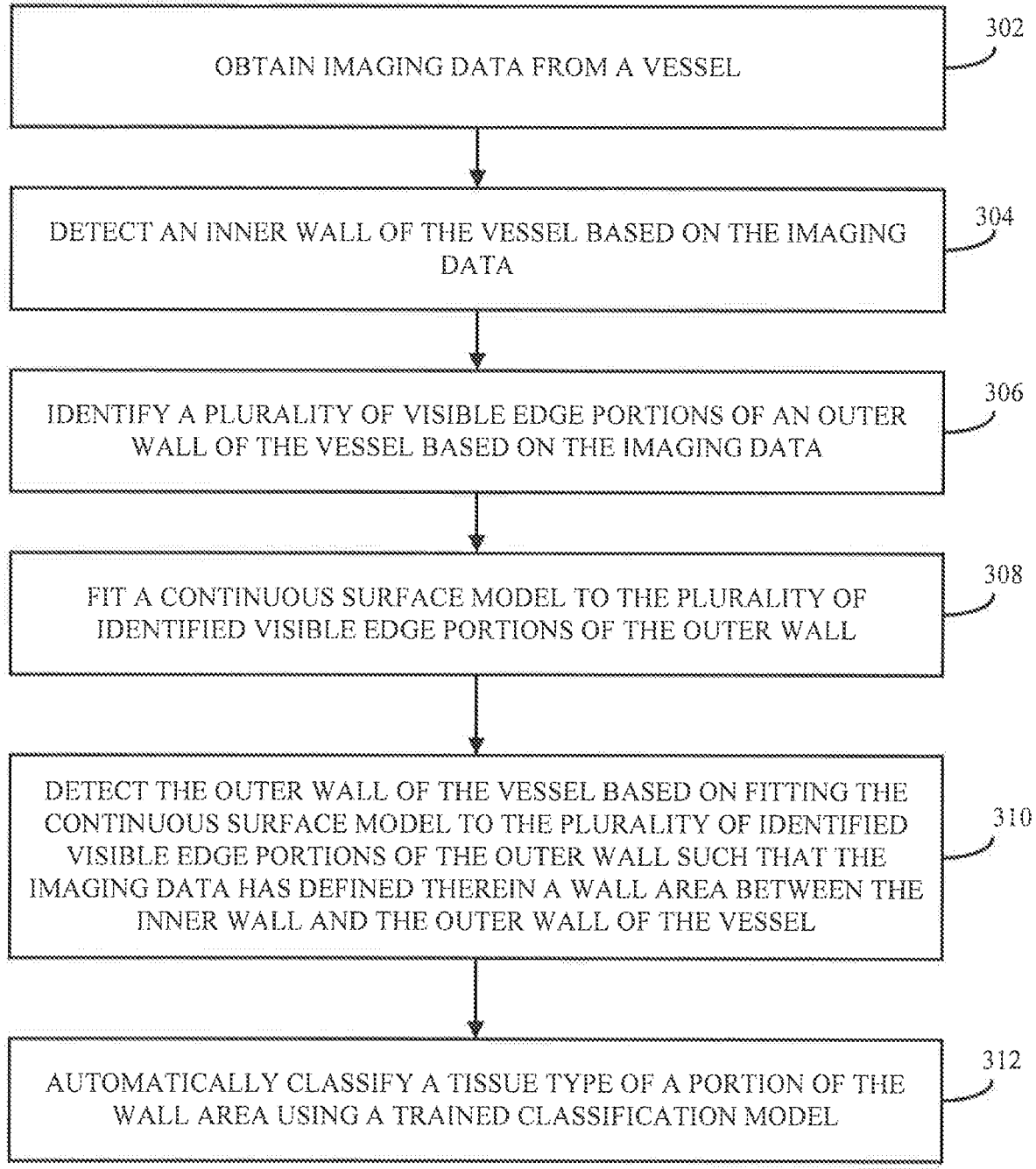
FIG. 3 illustrates an example method for generating a tissue classification map from acquired medical images in accordance with an embodiment.

As mentioned above, the classification maps 102 and 206 may be generated using various known methods. FIG. 3 illustrates an example method for generating a classification map from acquired medical images in accordance with an embodiment. The method illustrated in FIG. 3 is also described in U.S. patent application Ser. No. 16/415,430, entitled "Arterial Wall Characterization In Optical Coherence Tomography Imaging" and filed May 17, 2019 and publication L. S. Athanasiou, M. L. Olender, J. M. de la Torre Hernandez, E. Ben-Assa, and E. R. Edelman, "A deep learning approach to classify atherosclerosis using intracoronary optical coherence tomography," in *Medical Imaging 2019: Computer-Aided Diagnosis*, 2019, p. 22, both of which are herein incorporated by reference in their entirety. In the method illustrated in FIG. 3, a vessel wall area delineation procedure is used in conjunction with a trained classification model based on deep learning or other artificial intelligence methods (e.g., a neural network, a convolutional neural network (CNN), a support vector machine, a random forest, etc.) to identify and classify the composition of material within the identified arterial walls based on data obtained from, for example, an interferometric imaging method such as OCT.

At block 302, imaging data is obtained from a vessel, for example, by using an OCT imaging system. The imaging data may be, for example, a series of cross-sectional OCT images of the vessel. In other embodiments, imaging data from other types of imaging systems may be used such as, for example, ultrasound imaging (including intravascular ultrasound imaging), CT imaging, X-ray imaging, MR imaging, etc. At block 304, an inner wall of the vessel is detected based on the imaging data. At block 306, a plurality of visible edge portions of an outer wall of the vessel are identified based on the imaging data. At block 308, a continuous surface model is fit to the plurality of identified visible edge portions of the outer wall. At block 310, the outer wall of the vessel is detected based on fitting the continuous surface model to the plurality of identified visible edge portions of the outer wall such that the imaging data has defined therein a wall area between the inner wall and the outer wall of the vessel. Wall area is defined as the area between the lumen and outer border, i.e., the media-adventitia transition. At block 312, a tissue type of a portion of the wall area is automatically classified using a trained classification model. In an embodiment, the trained classification model may subdivide the arterial wall area into up to six different classes including one or more of calcium, lipid tissue, fibrous tissue, mixed tissue, non-pathological tissue or media, and no visible tissue. As mentioned above, the trained classification model may be based on deep learning or other artificial intelligence methods such as, for example, a CNN. The wall area as well as one or more tissue types that have been identified in the imaging data may be transmitted and/or provided to a user (e.g., an operator, a clinician, etc.) using, for example, a display, and/or stored (e.g., as part of a medical record associated with the subject) in, for example, data storage of a computer system.

Figure 4:
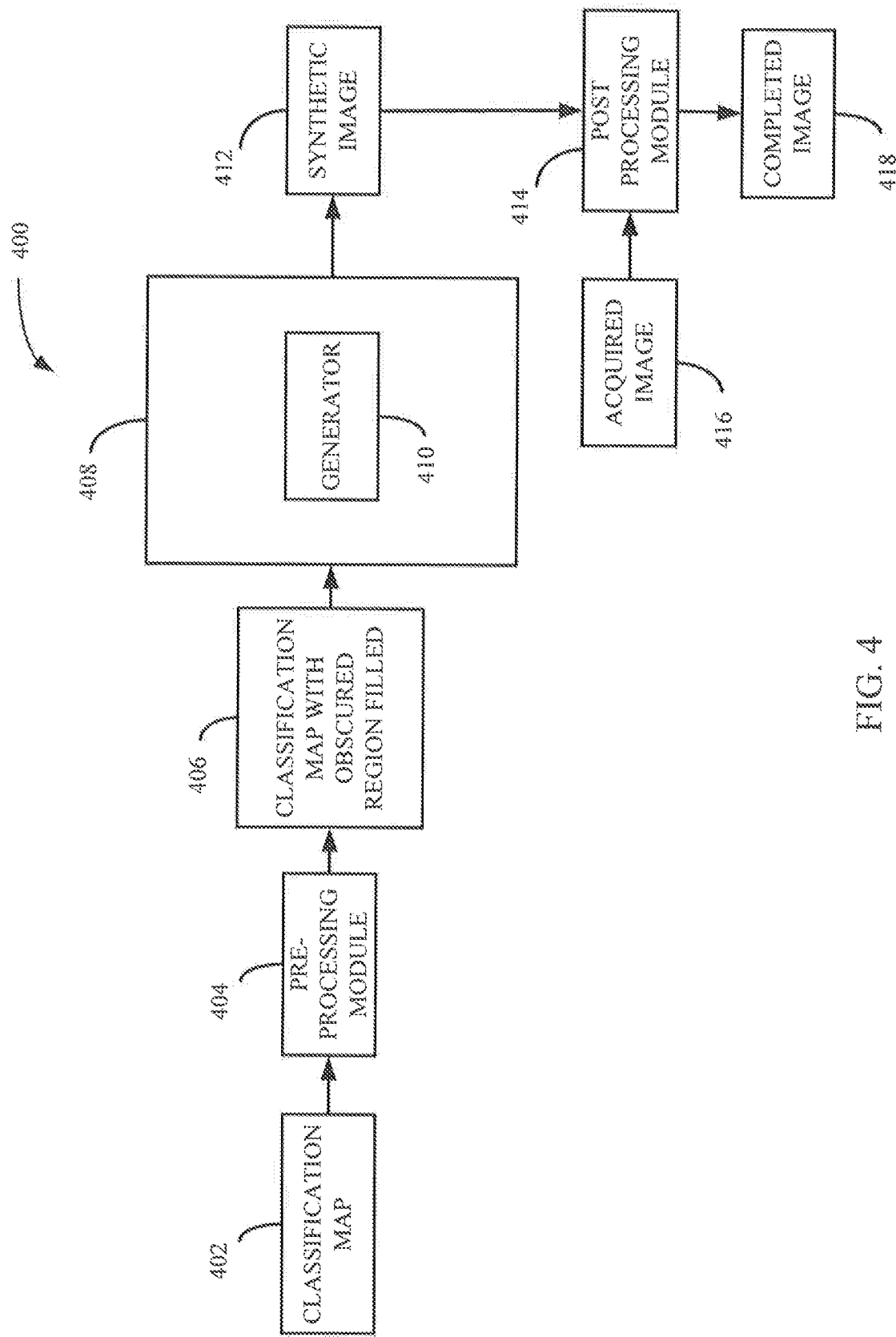
FIG. 4 is a block diagram of a system for completion of an acquired image using a synthesized image in accordance with an embodiment.

In one embodiment, a system for generating images using a trained generative network (e.g., system 100 shown in FIG. 1) may be utilized to complete an incomplete or partial image (i.e., an image with obscured region(s), e.g., a shadowed region). As used herein, the term "obscured" will be used to refer to obscured, obfuscated or shadowed regions in an image. For example, typically an intravascular OCT image includes an obscured region due to the presence of a guidewire used by an OCT system during the intravascular OCT imaging process. Any tissue that is distal to a proximal surface of a guidewire is cast in a shadow and appears dark due to the inability for signal to penetrate the metal guidewire. In another example, blood attenuates the optical signal of OCT and is typically flushed from the vessel prior to and throughout imaging. Residual blood (e.g., resulting from insufficient flush) can therefore similarly obscure tissue that is distal to the blood from the imaging catheter. FIG. 4 is a block diagram of a system for completion of an acquired image using a synthesized image in accordance with an embodiment. In FIG. 4, the system 400 includes a pre-processing module 404, a trained generative network 408, and a post-processing module 414. A classification map 402 is input into the pre-processing module 404. The classification map 402 is a classification map corresponding to an acquired image 416 acquired using an imaging system, for example, an OCT image acquired with an OCT system, and may be generated, for example, using the method described above with respect to FIG. 3. The acquired image 416 corresponding to the classification map 402 includes an obscured region (e.g., a shadow) caused by, for example, the presence of a guidewire. The classification map may be retrieved, for example, from data storage (or memory) of an imaging system (e.g., an OCT system) or other computer system. The pre-processing module 404 creates an obscured region mask based on the classification map 402. In another embodiment, the obscured region mask may be constructed based on an acquired image 416. Known methods may be used to generate the obscured region mask from the classification map or acquired image. The obscured region mask provides a designation of where the obscured region is present in the classification map or acquired image. The obscured region mask may be used to identify a pixel classification to be revised (e.g., because the initial classification in the obscured region is presumed to be unreliable). The pre-processing module 404 then generates and outputs a classification map 406 that has the obscured region filled in. For example, the pre-processing module 404 may determine the expected, likely, or nominal classifications of obscured pixels (e.g., through region growing and/or iterative mode filtering) which may be used to fill or replace the obscured region in the classification map 402. The classification map 406 with the filled in obscured region is provided as an input to a trained generative network such as, for example, generative network 104 shown in FIG. 1.

The trained generative network 408 (including generator 410) generates a synthetic image 412 based on the classification map 406. For example, the generator 410 of generative network 408 may receive the classification map 406 and generate an OCT image 412 based on the classification map 406. Post-processing module 414 receives as input the synthetic image 412 and the acquired image 416 that corresponds to the classification map 402. The acquired image 416 may be retrieved, for example, from data storage of an imaging system (e.g., an OCT system) or other computer system. The obscured region mask may be used to identify the pixels in the acquired image to be replaced by those in a generated image. Post-processing module 414 replaces the obscured pixels (e.g., the shadow) of the acquired image 416 with the corresponding pixels of the generated image 412 to create a completed image 418. In another embodiment, the full synthetic image 412 itself may be utilized instead of substituting specific pixels if the generated image 412 is of sufficient quality. In this embodiment, an obscured region mask does not need to be created and the synthetic image 412 may be generated by the generator 410 based on the original classification map 402 or a classification map 406 with the obscured region filled in without use of an obscured region mask. The completed image 418 may also be provided to and displayed on a display.

Figure 5:
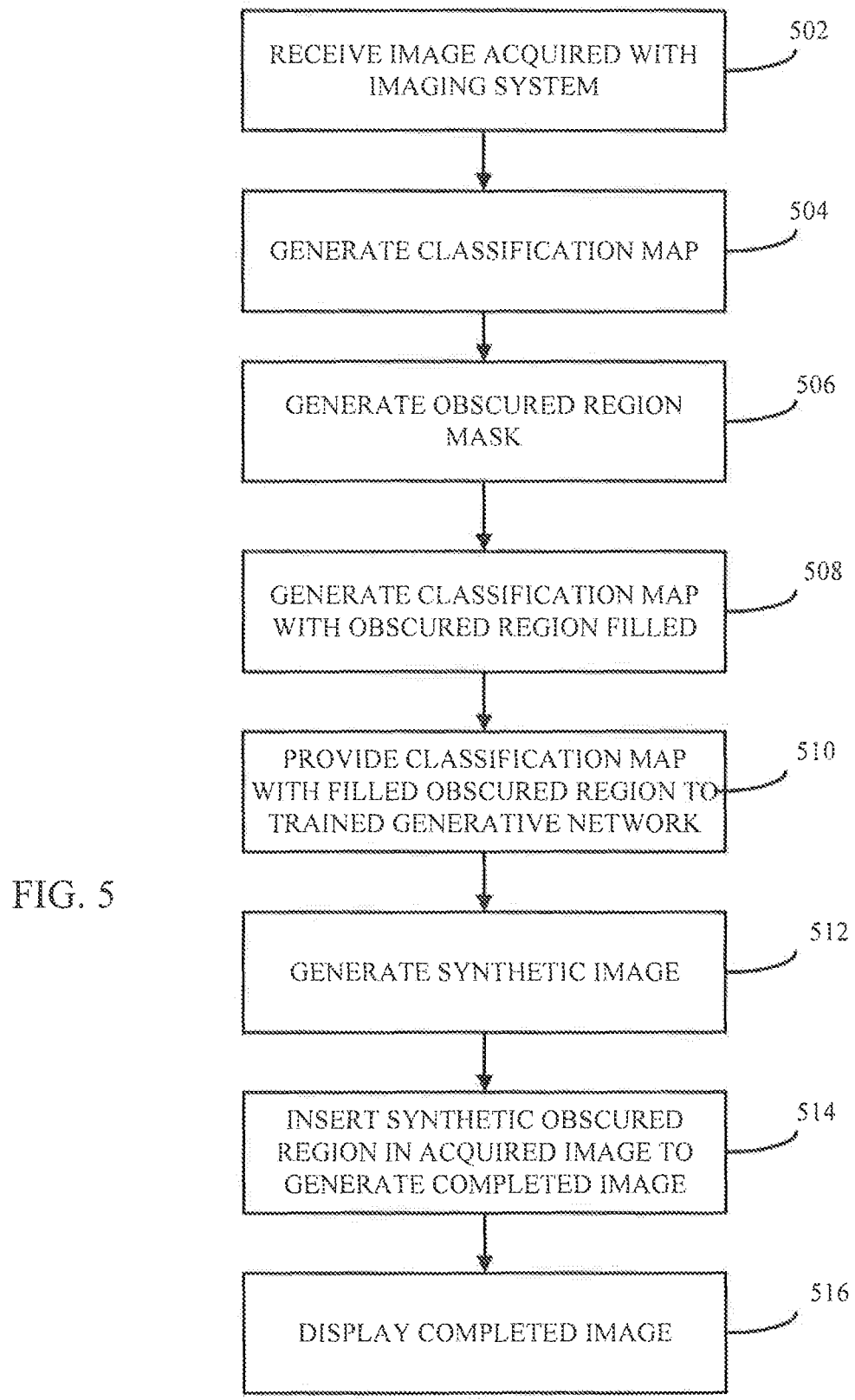
FIG. 5 illustrates a method for completing an acquired image using a synthesized image in accordance with an embodiment.

FIG. 5 illustrates a method for completing an acquired image using a synthesized image in accordance with an embodiment. At block 502, a medical image (e.g., an OCT image) that was acquired using an imaging system (e.g., an OCT system) is received, for example, from the imaging system or data storage. The acquired image includes an obscured region caused by, for example, the presence of a guidewire. At block 504, a classification map is generated based on the acquired image using, for example, the method described above with respect to FIG. 3. The classification map or an acquired image may then be used to create an obscured region mask at block 506. Known methods may be used to generate the obscured region mask from the classification map or acquired image. The obscured region mask provides a designation of where the obscured region is present in the classification map or acquired image. The obscured region mask may be used to identify a pixel classification to be revised (e.g., because the initial classification in the obscured region is presumed to be unreliable). At block 508, the obscured region in the classification map is filled in. For example, the expected, likely, or nominal classifications of obscured pixels (e.g., through region growing and/or iterative mode filtering) may be determined and used to fill the obscured region in the classification map. At block 510, the classification map with the filled in obscured region is provided to a trained generative network (e.g., generative network 104 shown in FIG. 1). At block 512, the trained generative network generates a synthetic OCT image based on the classification map with the filled in obscured region. At block 514, the synthetic OCT image may be used to complete the acquired OCT image that was used to generate the classification map. The obscured region mask may be used to identify the pixels in the acquired image to be replaced by those in a generated image. In one embodiment, the obscured pixels (e.g., a shadow) of the acquired image may be replaced with the corresponding pixels of the generated image to create a completed image. In another embodiment, the full synthetic image itself may be utilized instead of substituting specific pixels if the generated image is of sufficient quality. In this embodiment, an obscured region mask (block 506) may not need to be created. The completed image may also be provided to and displayed on a display at block 516.

Figure 6:
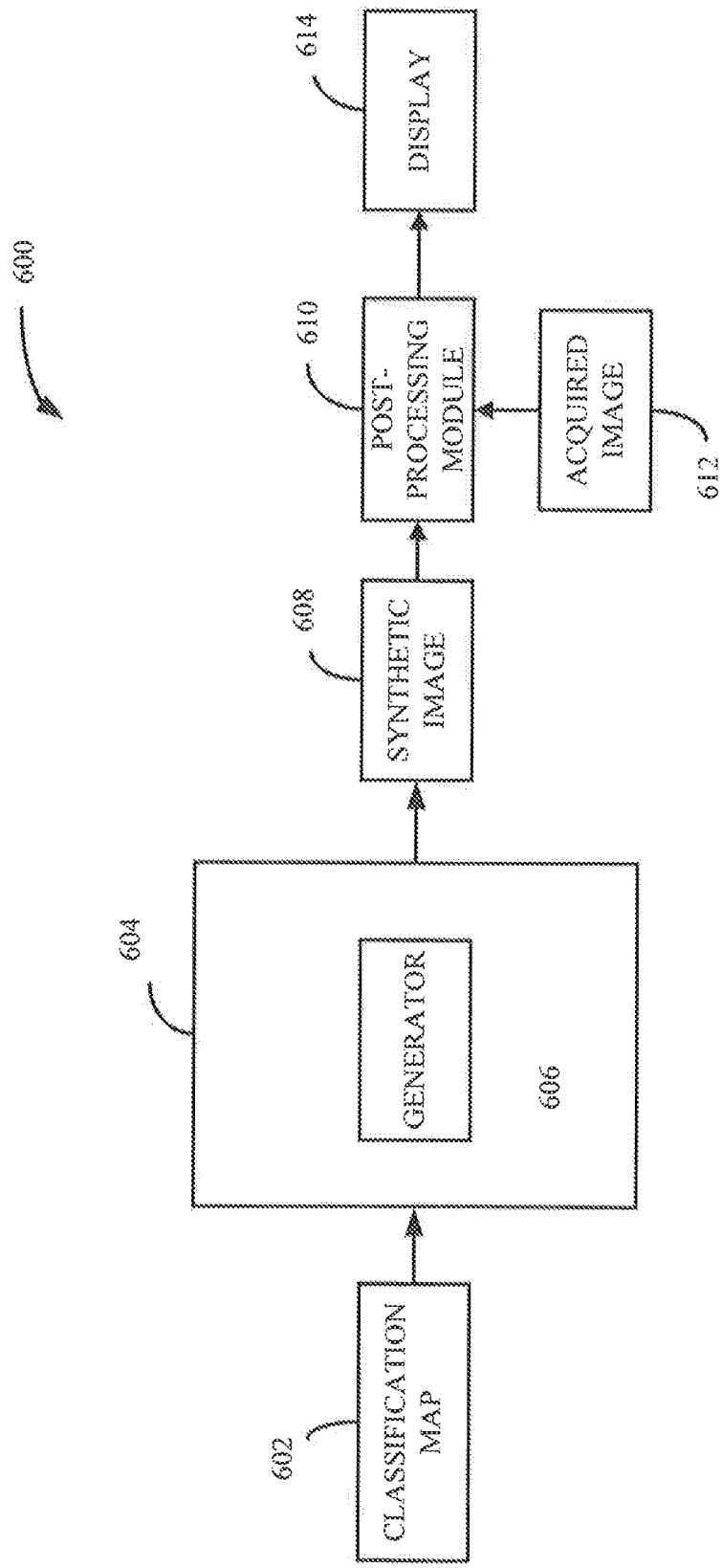
FIG. 6 is a block diagram of a system for identifying characteristics of a region of interest of a subject in an acquired image in accordance with an embodiment.

In another embodiment, a system for generating images using a trained generative network (e.g., system 100 shown in FIG. 1) may be utilized to identify at least one characteristic of a region of interest of a subject in an acquired image (e.g., tissue characteristics) that may manifest as abnormalities or deviations in the acquired image from the expected (as represented by the synthetic image generated using the generative network) or alternatively, a characteristic that may be confirmed by consistency between the acquired image and the generated image. The identified characteristic(s) may assist clinicians making diagnoses and providing clinical care. FIG. 6 is a block diagram of a system for identifying characteristics of a region of interest of a subject in an acquired image in accordance with an embodiment. In FIG. 6, the system 600 includes a trained generative network 604, a post-processing module 610 and a display 614. A classification map 602 is input into the generative network 604 (e.g., generative network 104 shown in FIG. 1). The classification map 602 may be a classification map of, for example, an intravascular image such as an OCT image (e.g., acquired with an OCT system) and may be generated, for example, using the method described above with respect to FIG. 3. The classification map may be retrieved, for example, from data storage (or memory) of an imaging system (e.g., an OCT system) or other computer system. The trained generative network 604 (including a generator 606) generates a synthetic image 608 (e.g., an intravascular image such as OCT image) based in the classification map 602. For example, the generator 606 of generative network 604 may receive the classification map 602 and generate an OCT image 608 based on the classification map 602. Post-processing module 610 receives as input the synthetic image 608 and an acquired image 612 of the same physical segment. The acquired image 612 may be retrieved, for example, from data storage of an imaging system (e.g., an OCT system) or other computer system. Post-processing module 610 compares the synthetic image 608 to the acquired image 612 of the same physical segment in order to highlight unexpected findings and potential abnormalities. For example, the synthetic image 608 (generated based upon standard presentation of the patient's given morphology) and the acquired image 612 (reflecting the actual presentation of the patient's morphology) may be directly compared through pixel-wise subtraction or similar processing to highlight unexpected findings and potential abnormalities warranting attention and further review. The comparison results may be provided to and displayed on the display 614.

Figure 7:
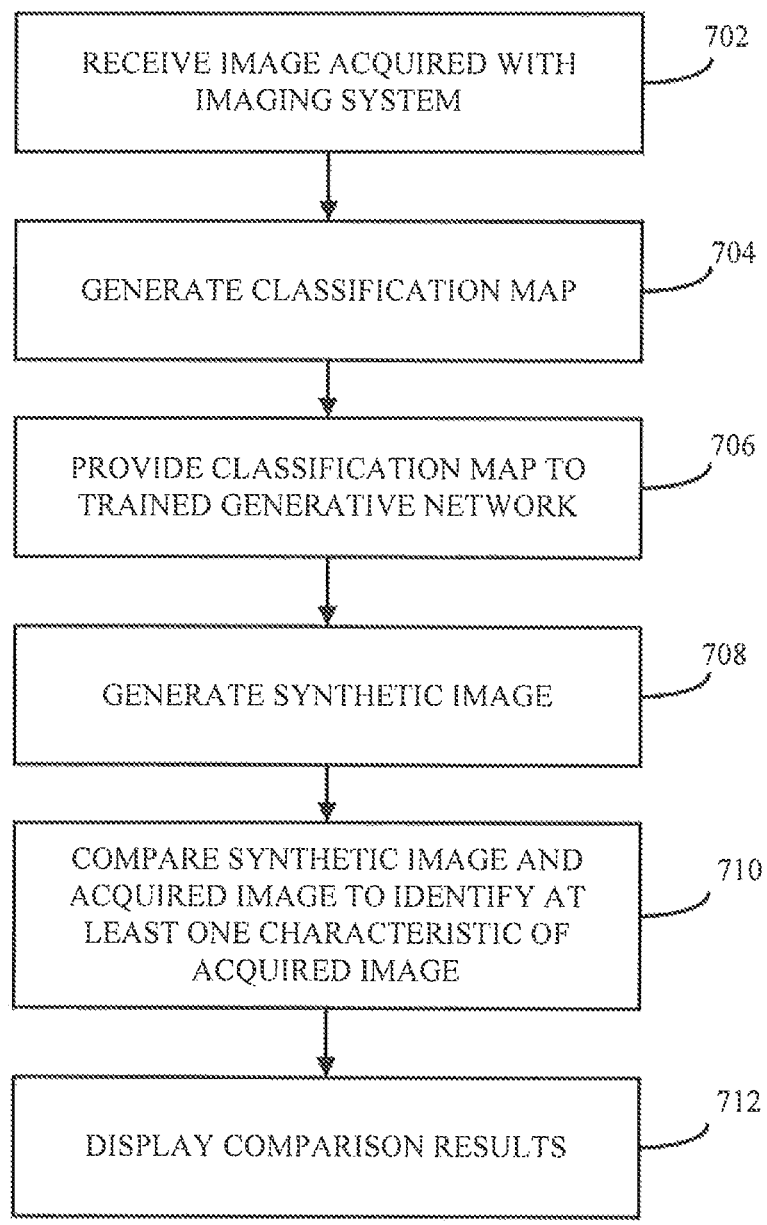
FIG. 7 illustrates a method for identifying characteristics of a region of interest of a subject in an acquired image in accordance with an embodiment.

FIG. 7 illustrates a method for identifying characteristics of a region of interest of a subject in an acquired image in accordance with an embodiment. At block 702, a medical image (e.g., an intravascular image such as an OCT image) that was acquired using an imaging system (e.g., an OCT system) is received, for example, from the imaging system or data storage. At block 704, a classification map may be generated based on the acquired image using, for example, the method described above with respect to FIG. 3. At block 706, the classification map is provided to a trained generative network (e.g., generative network 104 shown in FIG. 1). At block 708, the trained generative network generates a synthetic image (e.g., an intravascular image such as OCT image) based on the classification map. At block 710, the synthetic image is compared to an acquired (or real) image of the same physical segment in order to highlight unexpected findings and potential abnormalities. For example, the synthetic image (generated based upon standard presentation of the patient's given morphology) and the acquired image (reflecting the actual presentation of the patient's morphology) may be directly compared through pixel-wise subtraction or similar processing to highlight unexpected findings and potential abnormalities warranting attention and further review. The comparison results may be provided to and displayed on a display at block 712.

Figure 8:
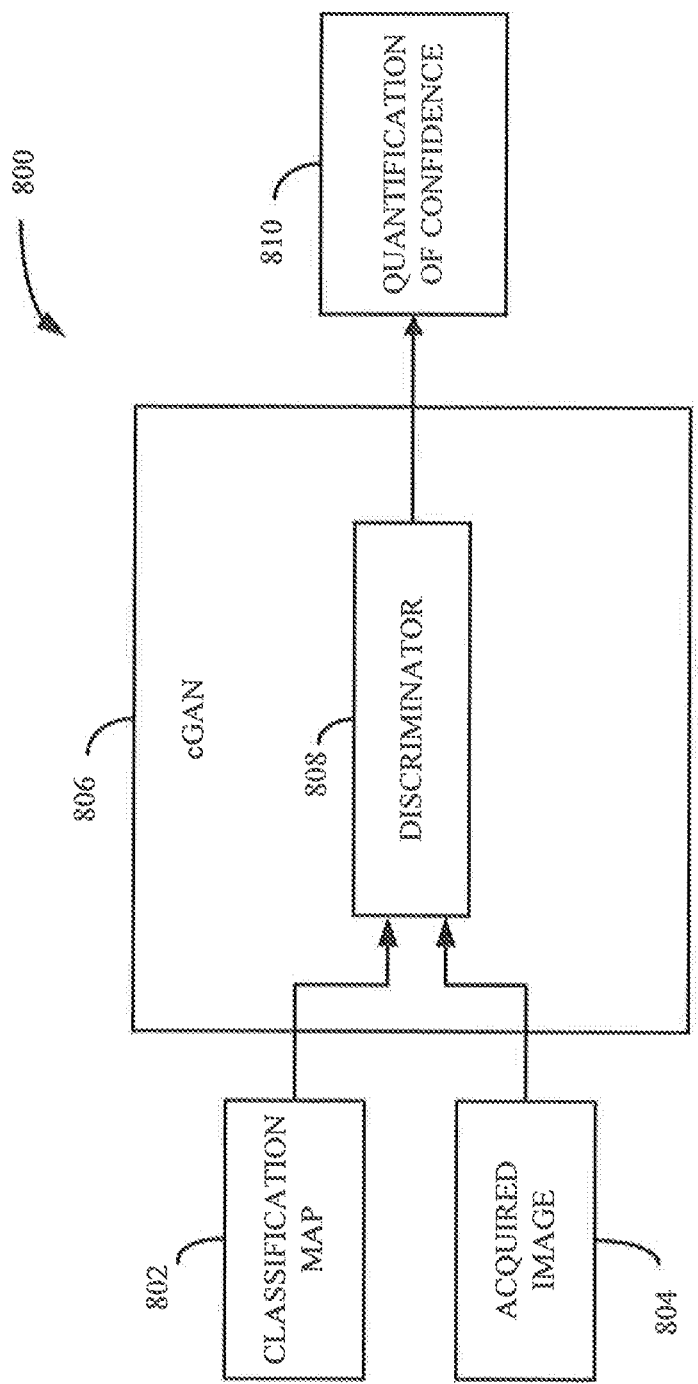
FIG. 8 is a block diagram of a system for quantifying confidence in a characterization or classification method in accordance with an embodiment.

In another embodiment, a trained discriminative network (e.g., discriminator 212 shown in FIG. 2) may be utilized to quantify confidence in (preceding) characterization or classification of images. FIG. 8 is a block diagram of a system for quantifying confidence in a characterization or classification method in accordance with an embodiment. In FIG. 8, the system 800 includes a trained discriminative network 806 which includes a trained discriminator 808. The discriminative network 806 may be trained using known methods. In one embodiment, the discriminative network 806 may be trained using a conditional generative adversarial network such as cGAN 200 described above with respect to FIG. 2. A classification map 802 and an acquired (real) image 804 are input into the discriminative network 806, in particular, the classification map 802 and acquired image 804 are input to the discriminator 808 of the discriminative network 806. In one embodiment, the classification map 802 may be a classification map of an OCT image (e.g., acquired with an OCT system) and may be generated using known methods. The classification map 802 and the acquired image 804 may be retrieved, for example, from data storage (or memory) of an imaging system (e.g., an OCT system) or other computer system. The discriminator 808 is trained to distinguish fake images from real images based upon a provided classification map. The fake or real determinations of the discriminator 808 of the discriminative network 806 may be used to quantify confidence in a classification or characterization method. The output 810 (i.e., a quantification of confidence) of the discriminator 808 reflects the accuracy of the characterization method. If classification is performed well, the original image should always be discriminated as "real," while error in the classification will result in "fake" discrimination (or less certainty/confidence, i.e., lower probability, in the "real" determination). The quantification of confidence 810 output may be provided to and displayed on a display. In another embodiment, the confidence in a classification method may be quantified by comparing a synthetic image generated by a generative network (e.g., generative network 104 shown in FIG. 1) and an actual image (upon which the characterization process was performed), for example, through summed square of intensity differences or summed absolute intensity deviation.

Figure 9:
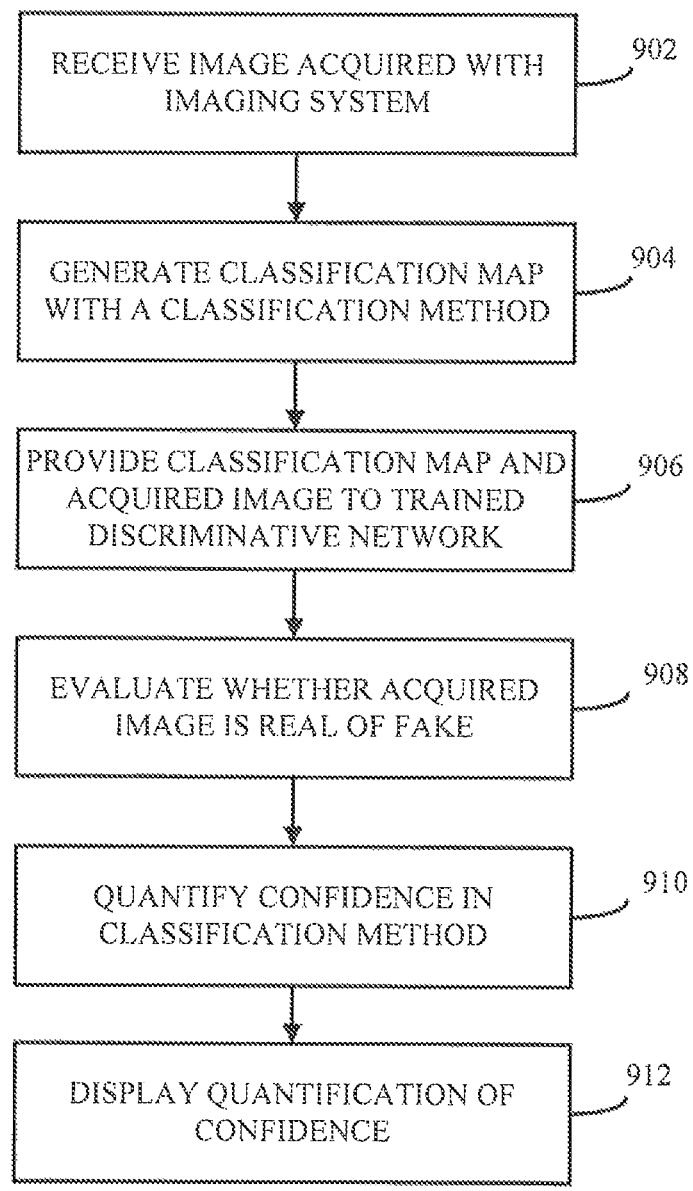
FIG. 9 illustrates a method for quantifying confidence in a characterization or classification method in accordance with an embodiment.

FIG. 9 illustrate a method for quantifying confidence in a characterization or classification method in accordance with an embodiment. At block 902, a medical image (e.g., an OCT image) that was acquired using an imaging system (e.g., an OCT system) is received, for example, from the imaging system or data storage. At block 904, a classification map is generated based on the acquired image using, for example, known image classification methods. At block 906, the classification map and the acquired image are provided to a trained discriminative network (e.g., discriminative network 806 shown in FIG. 8) and in particular, the classification map and acquired image are input to a discriminator. The classification map and the acquired image may be retrieved, for example, from data storage (or memory) of an imaging system (e.g., an OCT system) or other computer system. The discriminator evaluates whether the acquired image is real or fake based upon the provided classification map at block 908. The fake or real determinations of the discriminator may be used to quantify confidence in a classification or characterization method at block 910. The output (i.e., a quantification of confidence) of the discriminator reflects the accuracy of the characterization method. If classification is performed well, the original image should always be discriminated as "real," while error in the classification will result in "fake" discrimination (or less certainty/confidence, i.e., lower probability, in the "real" determination). At block 912, the quantification of confidence output may be provided to and displayed on a display.

In another embodiment, a system for generating images using a trained generative network (e.g., system 100 shown in FIG. 1) may be utilized to determine an image manifestation of clinical outcomes for rapid and direct verification of an outcome state in the clinical setting. In this embodiment, a characterized (or classified) image may be used to construct a model system, for example, a finite element model. The model system may then be perturbed (or deformed), for example, by a simulated deployment of an interventional device. Various iterations may be performed to generate multiple simulated procedures, interventions or tests (i.e., perturbed model systems) carried out with various parameters (e.g., device placement, settings, etc.). As used herein, the term "procedure" will be used to refer to a procedure, intervention, or test. Synthetic images for the simulated modified/perturbed model system(s) may be generated using a trained generative network (e.g., generative network 104 shown in FIG. 1). In one embodiment, the synthetic images generated based on the simulated modified/perturbed model system may be offered to clinicians and may provide a glimpse into what a successful or unsuccessful deployment (or intervention) for a given patient would look like. Among other uses, the resulting synthetic images may also be used for selecting parameters and planning treatment. In another embodiment, this method may be used to generate images in cases where the deployed device precludes actual imaging.

Figure 10:
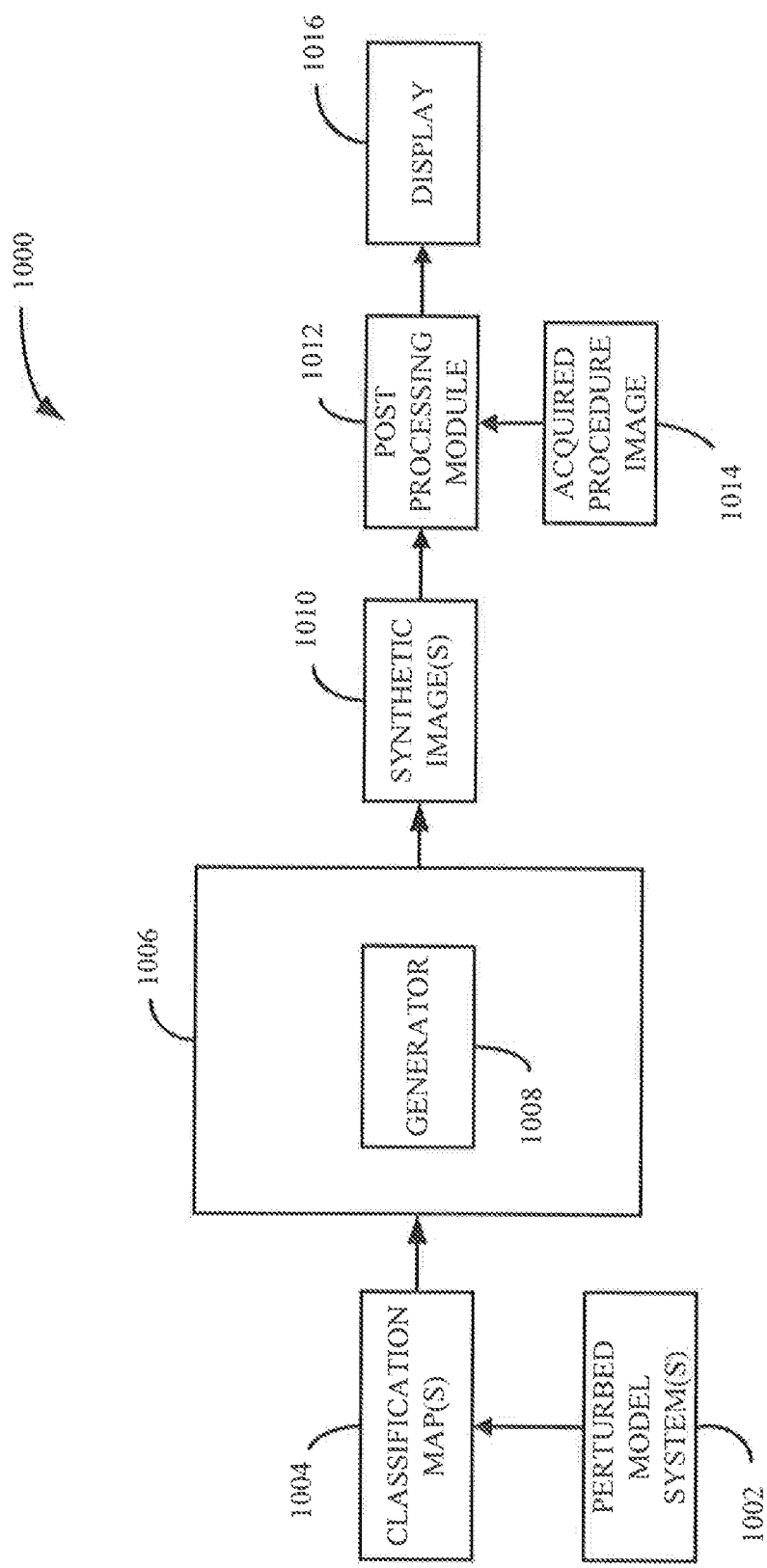
FIG. 10 is a block diagram of a system for determining a parameter or material property associated with a procedure in accordance with an embodiment.

In yet another embodiment, the synthetic images generated based on the simulated perturbed model system may allow for easy evaluation of a procedure once the real device is deployed (or other intervention undertaken) and imaging acquired and enable faster assessment and decision-making in the operating theater. For example, the resulting synthetic images may be compared to real images acquired following the real procedure to determine post hoc which parameters or state conditions were implemented or present in the procedure or to identify material properties of, for example, a tissue, organ, or vessel during or after the procedure. FIG. 10 is a block diagram of a system for determining a parameter or material property associated with a procedure in accordance with an embodiment. In FIG. 10, the system 1000 includes a trained generative network 1006, a post-processing module 1012 and a display 1016. A classification map 1004 is input into the generative network 1006 (e.g., generative network 104 shown in FIG. 1). In an embodiment, the classification map 1004 is associated with a perturbed model system 1002. For example, the perturbed model system 1002 may be generated using images (e.g., OCT images) of a region of interest of a subject acquired with an imaging system (e.g., an OCT system) before a procedure or intervention is performed. The perturbed model system 1002 and the pre-procedure images may be stored in or retrieved from, for example, data storage (or memory) of an imaging system or other computer system. In an embodiment, a pre-procedure classification map may be generated based on an acquired pre-procedure image. The pre-procedure classification map may be a classification map of an OCT image (e.g., acquired with an OCT system) and may be generated, for example, using the method described above with respect to FIG. 3. A model system is then generated using the pre-procedure images. In another embodiment, the pre-procedure classification map may also be used to generate the model system. The model system may be, for example, a finite element model or computational fluid dynamics model and the model system may be generated using known methods. One or more perturbed (or deformed) model systems 1002 may then be generated by conducting a parametric analysis using the model system. For example, various simulations may be run with the model system with different parameters to generate one or more perturbed model systems 1002. The parameters may be related to the procedure, for example, a position of a device, pressure of a stent-deploying balloon, etc., or related to properties of the tissues, organs, or vessels in the region of interest. Each perturbed model system 1002 may include an embedded classification map. The classification map 1004 from a perturbed model system 1002 may be extracted and input into the generative network 1006. The classification map 1004 may be retrieved, for example, from data storage (or memory) of an imaging system (e.g., an OCT system) or other computer system.

The trained generative network 1006 (including a generator 1008) generates a synthetic image 1010 based in the classification map 1004. For example, the generator 1008 of generative network 1006 may receive the classification map 1004 and generate an OCT image based on the classification map 1004. One or more synthetic images 1010 may be generated for each perturbed model system 1002 that has been generated for the procedure (i.e., for each set of parameters). Post-processing module 1012 receives as input the synthetic image(s) 1010. In addition, post-processing module 1012 receives an acquired procedure image 1014 that has been acquired for the region of interest of the subject after the procedure has been performed on the subject. In another embodiment, the acquired procedure image 1014 may be acquired during the procedure. The acquired procedure image 1014 may be retrieved, for example, from data storage of an imaging system (e.g., an OCT system) or other computer system. Post-processing module 1012 compares the synthetic images 1010 to the acquired procedure image 1014 to determine the synthetic image or images 1010 that best match the acquired procedure image 1014. The comparison of the synthetic images 1010 and the acquired procedure image 1014 to determine a match may be performed using known methods, for example, cross-correlation, and may integrate input from a human user. Parameters or material properties associated with the acquired procedure image (e.g., parameters and properties of the performed procedure and the tissues, organs, or vessels) may be determined based on the parameters and material properties associated with the synthetic image most similar to the acquired procedure image. As mentioned, each generated synthetic image 1010 has an associated set of parametric states and may have an associated clinical state. The associated set of parametric states are the parameters and properties which produced the perturbed model system which served as the basis for the synthetic image. The identified parameters and material properties may be provided to and displayed on the display 1016 or stored in a memory (not shown). The identified parameters and material properties may be used in a subsequent procedure or used to determine next steps during a procedure.

Figure 11:
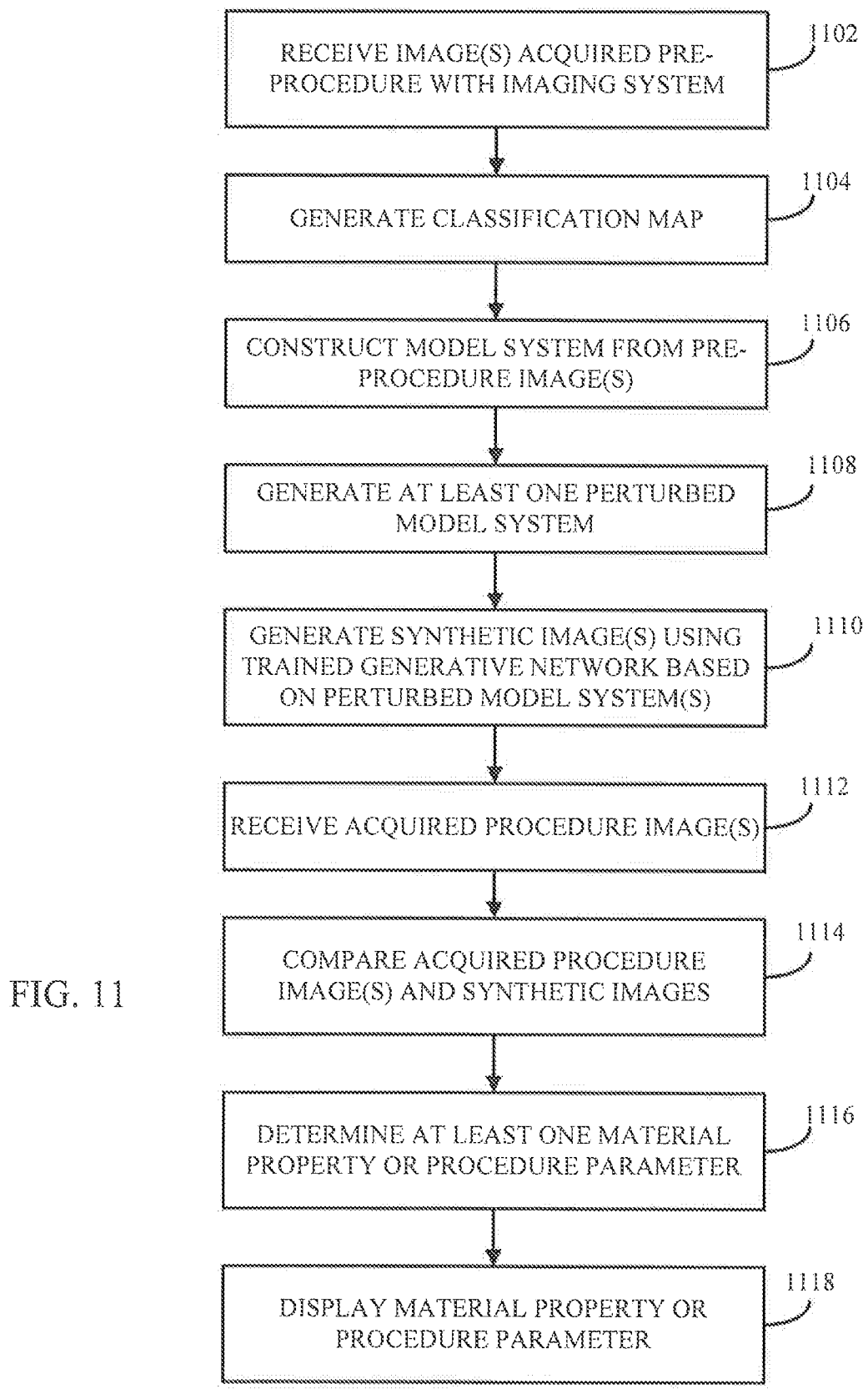
FIG. 11 illustrates a method for determining a parameter or material property associated with a procedure in accordance with an embodiment.

FIG. 11 illustrates a method for determining a parameter or material property associated with a procedure in accordance with an embodiment. At block 1102, images (e.g., OCT images) of a region of interest of a subject acquired with an imaging system (e.g., an OCT system) before performing a procedure or intervention are received, for example, from the imaging system or data storage. At block 1104, a pre-procedure classification map may be generated based on an acquired pre-procedure image using known methods. In an embodiment, the pre-procedure classification map may be a classification map of an OCT image (e.g., acquired with an OCT system) and may be generated, for example, using the method described above with respect to FIG. 3. At block 1106, a model system is generated using the pre-procedure images. In another embodiment, the pre-procedure classification map may also be used to generate the model system. The model system may be, for example, a finite element model or computational fluid dynamics model and the model system may be generated using known methods. At block 1108, at least one perturbed (or deformed) model system is generated by conducting a parametric analysis using the model system. For example, various simulations may be run with the model system with different parameters to generate one or more perturbed model systems. The parameters may be related to the procedure, for example, a position of a device, pressure of a stent-deploying balloon, etc., or related to properties of the tissues, organs, or vessels in the region of interest. Each perturbed model system may include an embedded classification map. The perturbed model system may be stored in or retrieved from, for example, data storage (or memory) of an imaging system or other computer system. At block 1110, the classification map from a perturbed model system may be extracted and input into a trained generative network (e.g., generative network 1006 shown in FIG. 10) which generates a synthetic image based on the classification map associated with the perturbed model system. The classification map may be retrieved, for example, from data storage (or memory) of an imaging system (e.g., an OCT system) or other computer system. In an embodiment, one or more synthetic images may be generated for each perturbed model system that has been generated for the procedure (i.e., for each set of parameters).

At block 1112, an acquired procedure image or images are received, for example, from the imaging system, data storage, or other computer system. The acquired procedure images are images acquired for the region of interest of the subject after the procedure has been performed on the subject. In another embodiment, the acquired procedure image may be acquired during the procedure. At block 1114, the synthetic images are compared to an acquired procedure image to determine the synthetic image or images that best match the acquired procedure image. The comparison of the synthetic images and the acquired procedure image to determine a match may be performed using known methods, for example, cross-correlation, and may integrate input from a human user. Parameters or material properties associated with the acquired procedure image (e.g., parameters and properties of the performed procedure and the tissues, organs, or vessels) may be determined at block 1116 based on the parameters and material properties associated with the synthetic image most similar to the acquired procedure image. As mentioned, each generated synthetic image has an associated set of parametric states and may have an associated clinical state. The associated set of parametric states are the parameters and properties which produced the perturbed model system which served as the basis for the synthetic image. The identified parameters and material properties may be provided to and displayed on the display at block 1118 or stored in a memory (not shown). As mentioned, the identified parameters and material properties may be used in a subsequent procedure or used to determine next steps during a procedure.

In another embodiment, the image(s) generated by a system 100 shown in FIG. 1 may be utilized for education and training applications, particularly for medical students or continuing education for licensed professionals. The method for generating a medical image (e.g., an OCT image) based on a classification map described herein offers an unlimited source of sample images of nearly any conceivable physical scenario. In one example, OCT images may be generated with a plurality of various plaques in known locations within a displayed arterial cross-section. This allows for an infinite pool of inherently-labeled images for use in education and training. In the course of, for example, medical student training, professional certification or licensing exams, or continuing education courses, images can be generated and presented to a trainee, who would then be tasked with identifying the type and location of plaques, or performing diagnostic tasks.

In another embodiment, the image(s) generated by a system 100 shown in FIG. 1 may be utilized for model training or method evaluation (e.g., in research and development). In one example, OCT images may be generated with a plurality of various plaques in known locations within a displayed arterial cross-section. The generated images and labels may then be fed as an input into a computational or numerical model (e.g., a machine learning model) to train, test, validate, and/or otherwise optimize the model or image-processing method/technique.

In another embodiment, a system for generating images using a trained generative network (e.g., system 100 shown in FIG. 1) may be utilized for converting images between modalities using a classification map (e.g., a plaque map) intermediary. In one embodiment, the system converts from virtual histology (VH) intravascular ultrasound (IVUS) images to OCT images via a plaque map intermediary. VH-IVUS, as well as some validated machine learning methods using grayscale IVUS, may be used to generate tissue/plaque maps of arterial wall cross-sections. These maps may then be input into a trained cGAN to generate corresponding OCT images of the same wall segment. This allows for imaging datasets acquired with different modalities, potentially during different patient visits and/or at different medical centers, to be directly compared, and also for a clinician to review the conveyed morphological data in the visualization/representation of choice. This embodiment of the system for generating images may, for example, be integrated into (electronic) medical record systems and used to allow for "conversion" of arterial imaging data among various representations/modalities. This embodiment may also aide in clinical study/research data management by being used to loosen limitations regarding equipment and expertise for clinical center inclusion (e.g., if a center only has IVUS capabilities, but a study is seeking and utilizing OCT data to monitor clinical endpoints). In the same way, such a system could also be used to effectively normalize images acquired by different machines or operators but by the same modality.

In another embodiment, a system for generating images using a trained generative network (e.g., system 100 shown in FIG. 1) may be utilized for co-registration of imaging sequences of inconsistent modalities. Given two image sequences of the same vessel segment (or some common section thereof) acquired with different modalities, a trained generative network may be used to convert one image sequence to the other via a classification map (e.g., a plaque map) intermediary such that both imaging sequences are visualized as if they were acquired by the same modality (e.g., OCT). The two sequences could then more readily and successfully be co-registered (corresponding frames can be identified), e.g., by maximizing cross-correlation between the two along the longitudinal axis or by displaying both sets of images (visualized as if acquired by the same modality) and soliciting input from a human user. The results provide a one-to-one matching of the frames of one series to those in another.

Figure 12:
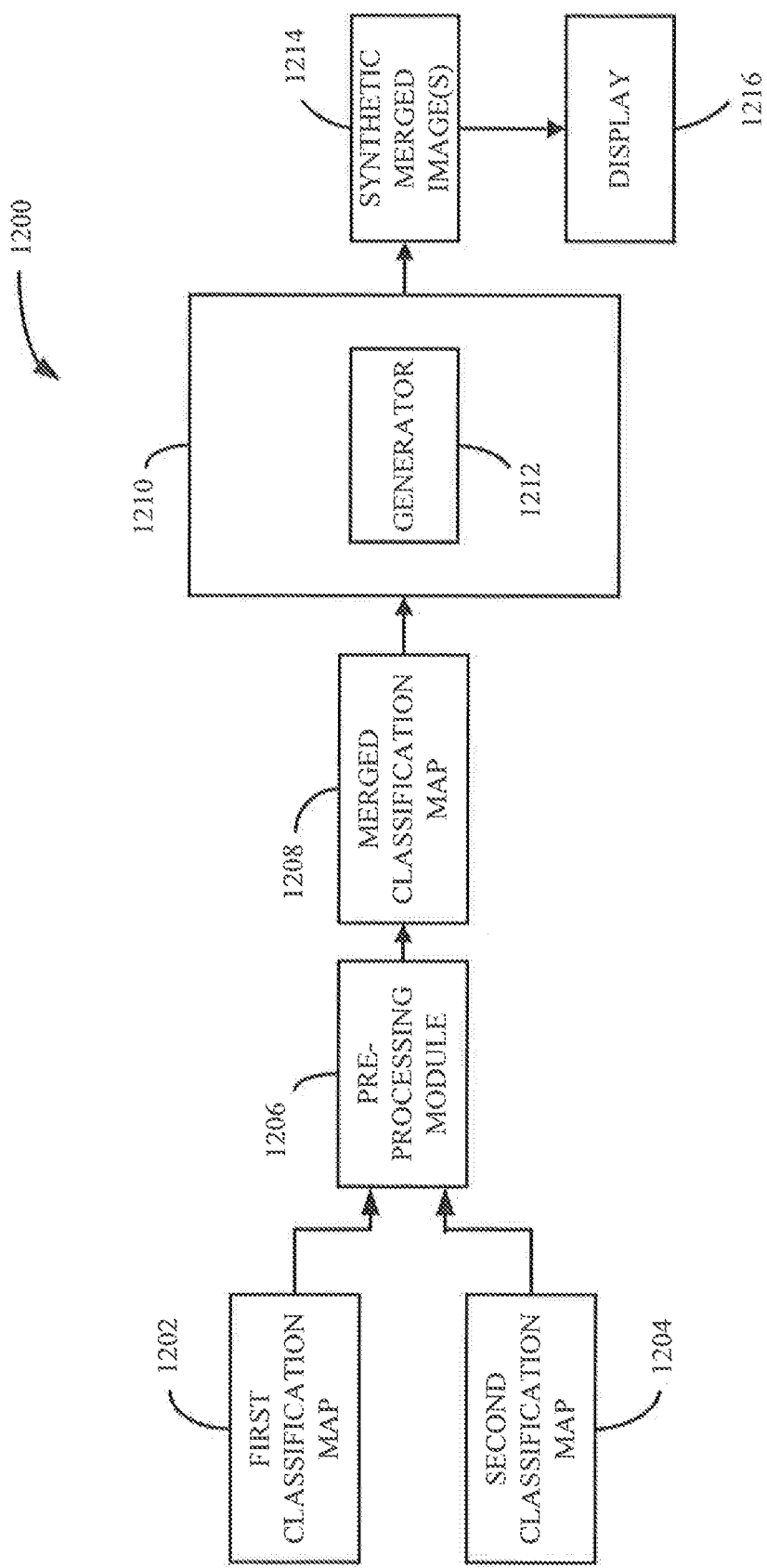
FIG. 12 is a block diagram of a system for merging two or more acquired images of a subject in accordance with an embodiment.

In another embodiment, a system for generating images using a trained generative network (e.g., system 100 shown in FIG. 1) may be utilized to merge and display information from a plurality of acquired images (e.g., images of the same physical segment acquired with different imaging modalities). FIG. 12 is a block diagram of a system for merging two or more acquired images of a subject in accordance with an embodiment. In FIG. 12, the system 1200 includes a pre-processing module 1206 and a trained generative network 1210. A first classification map 1202 and a second classification map 1204 are input into the pre-processing module 1206. While two classification maps 1202, 1204 are shown in FIG. 12, it should be understood that in other embodiments, more than two classification maps may be input to the pre-processing module 1206. The first classification map 1202 corresponds to a first acquired image acquired using an imaging system and the second classification map 1204 corresponds to a second acquired image acquired using an imaging system. In an embodiment, the acquired images corresponding to the classification maps are images of the same physical segment. In an embodiment, the first acquired image and the second acquired image may be acquired using imaging systems associated with different imaging modalities and therefore, the first 1202 and second 1204 classification maps are associated with different imaging modalities. In other words, the first classification map is associated with a first imaging modality and the second classification map is associated with a second imaging modality and the first and second imaging modalities are different imaging modalities For example, the first classification map 1202 may correspond to an acquired image that is an OCT image (e.g., an intravascular image) acquired with an OCT system, while the second classification map 1204 may correspond to an acquired image that is an IVUS image acquired with an IVUS system. The first classification map 1202 and the second classification map 1204 may be generated, for example, using the method described above with respect to FIG. 3. In another embodiment, either the first and second classification maps may be derived from a source of data, such as a VH system integrated with an IVUS imaging system. In an embodiment where more than two classification maps are input into the pre-processing module, at least two of the three or more classification maps correspond to different imaging modalities. The acquired images that correspond to the classification maps may be acquired with different imaging systems or may be acquired by a single hybrid system employing multiple imaging or classification technologies and outputting multiple sets of such data where each set of data may be generated using a different technology of the hybrid system. The first classification map 1202 and the second classification map 1204 may be retrieved, for example, from data storage (or memory) of an imaging system (e.g., an OCT system) or other computer system.

The pre-processing module 1206 merges the plurality of classification maps (e.g., classification maps 1202 and 1204) into a single merged classification map 1208. Before merging the classification maps, the pre-processing module 1206 may be configured to align the first classification map 1202 and the second classification map 1204 using known methods for aligning images. In another embodiment, the acquired images used to generate the classification maps 1202 and 1404 may be aligned before the individual classification maps 1202 and 1204 are generated. The pre-processing module 1206 may use known methods to generate the merged classification map from the plurality of classification maps (e.g., the first classification map 1202 and the second classification map 1204). The single merged classification map 1208 generated by the pre-processing module 1206 includes information contained in one or more of the first or second acquired images corresponding to the first or second classification maps 1202, 1204. For example, the pre-processing module 1206 may consider the reliability of all classification maps at each spatial location, and in each region take the form of the classification map considered to be most reliable in that location, forming a composite of the two or more input classification maps. In an embodiment where more than two classification maps are input to the pre-processing module 1206, the merged classification map 1208 includes information contained in one or more of the more than two acquired images corresponding to the two or more classification maps. The merged classification map 1208 is provided as an input to a trained generative network 1210 such as, for example, generative network 104 shown in FIG. 1. The trained generative network 1210 (including generator 1212) generates a synthetic merged image 1214 based on the merged classification map 1208. For example, the generator 1212 of generative network 1210 may receive the merged classification map 1208 and generate an OCT image 1214 (e.g., n intravascular image) based on the merged classification map 1208. The synthetic merged image may also be provided to and displayed on a display 1216. The synthetic merged image 1214 may be used by a user (e.g., a clinician) to guide diagnosis, prognosis, and decision making. A synthetic merged image 1214 may facilitate the interpretation of imaging data through consolidation of disparate datasets into a single coherent dataset.

In another embodiment, the first classification map 1202 and the second classification map 1204 may be associated with the same imaging modality, i.e., the first classification map 1202 and the second classification map 1204 correspond to a first acquired image and a second acquired image that are acquired using the same imaging modality. For example, the system 1200 may be applied to a pair of OCT images (of the same vessel segment) in which, for example, the guidewire shadow is located in different positions in each of the OCT images to generate a synthetic merged image that combines the most reliable information from each OCT image. As mentioned above, the merged classification map 1208 generated by the pre-processing module 1206 may include information contained in one or more of the input classification maps (e.g., maps 1202, 1204). A merged classification map 1208 may only include information contained in one of the plurality of input classification maps if, for example, the pre-processing module 1206 utilizes information such as the tissue characterization confidence at each point and the selected classes with the highest degree of confidence are all from the same classification map.

Figure 13:
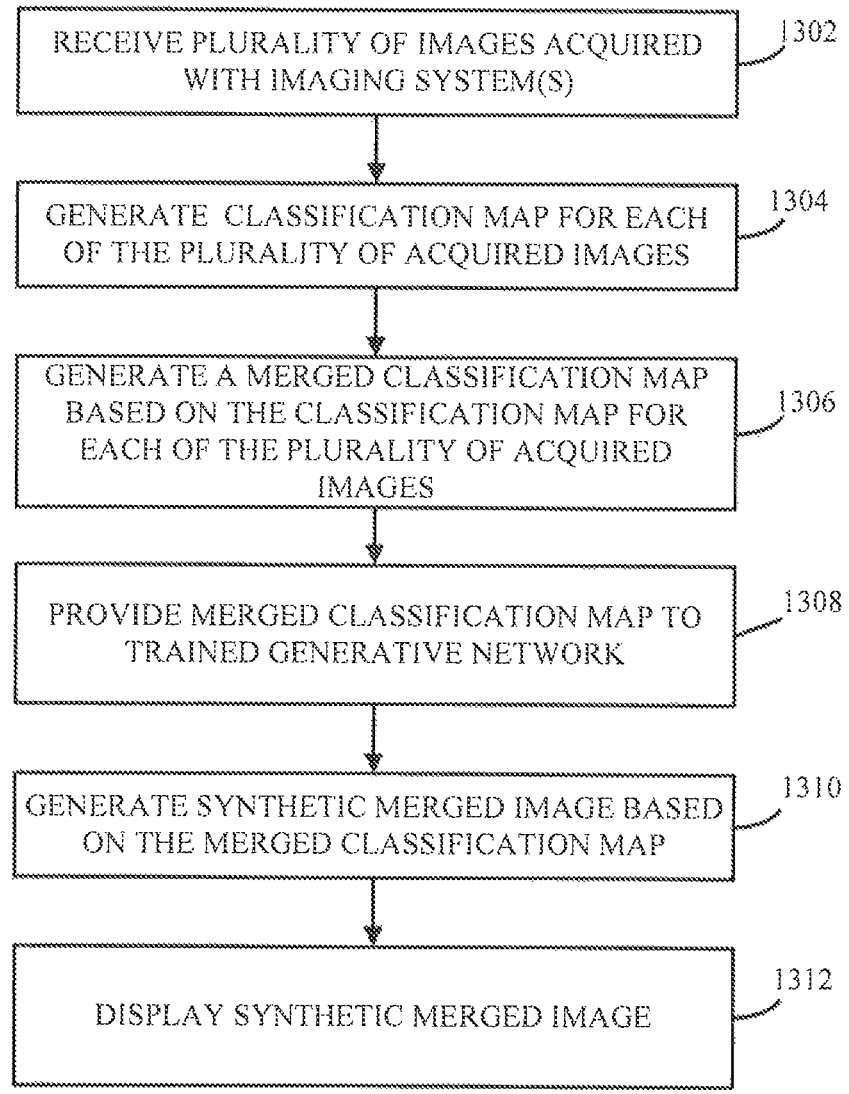
FIG. 13 illustrates a method for merging two or more acquired images of a subject in accordance with an embodiment.

FIG. 13 illustrates a method for merging a two of more acquired images of a subject in accordance with an embodiment. At block 1302, a plurality of medical images (e.g., intravascular OCT and IVUS images) that were acquired using one or more imaging systems (e.g., an OCT and IVUS system) is received, for example, from one or more imaging systems or data storage. At block 1304, a plurality of classification maps are generated where each of the plurality of classification maps are generated based on one of the plurality of acquired images. As discussed above with respect to FIG. 12, in one embodiment each of the plurality of acquired images are acquired using different imaging systems associated with different imaging modalities and therefore, each of the plurality of classification maps are associated with different imaging modalities. The plurality of classification maps may be generated using, for example, the method described above with respect to FIG. 3. In another embodiment, one or more of the plurality of classification maps may be derived from a source of data such as VH based directly on radiofrequency analysis. In an embodiment where the plurality of classification maps include more than two classification maps, at least two of the plurality of classification maps correspond to different imaging modalities The plurality of acquired images that correspond to the plurality of classification maps may be acquired with different imaging systems or may be acquired by a single hybrid system employing multiple imaging or classification technologies and outputting multiple sets of such data, where each set of data may be generated using a different technology of the hybrid system. At block 1306, the plurality of classification maps may then be used to create or generate a single merged classification map that merges the plurality of individual classification maps. Before merging the classification maps, the classification maps may be aligned using known methods for aligning images. In another embodiment, the acquired images used to generate the classification maps may be aligned before the individual classification maps are generated. Known methods may be used to generate the combined or merged classification map from the plurality of classification maps or acquired images. The generated merged classification map includes information contained in one or more of plurality of acquired images corresponding to the plurality of classification maps. For example, the reliability of all classification maps may be considered at each spatial location, and in each region the form of the classification map considered to be most reliable in that location may be retained, forming a composite of the two or more classification maps. At block 1308, the merged classification map with the combined information is provided to a trained generative network (e.g., generative network 104 shown in FIG. 1). At block 1310, the trained generative network generates a synthetic merged image based on the merged classification map with the combined information. For example, the synthetic merged image may be an OCT image (e.g., an intravascular image). The synthetic merged image may also be provided to and displayed on a display at block 1312. The synthetic merged image may be used by a user (e.g., a clinician) to guide diagnosis, prognosis, and decision making. A synthetic merged image may facilitate the interpretation of imaging data through consolidation of disparate datasets into a single coherent dataset.

In another embodiment, the plurality of classification maps may be associated with the same imaging modality, i.e., each classification map in the plurality of classification maps correspond to acquired images that are acquired using the same imaging modality. For example, the method for merging a plurality of images may be applied to a pair of OCT images (of the same vessel segment) in which, for example, the guidewire shadow is located in different positions in each of the OCT images to generate a synthetic merged image that combines the most reliable information from each OCT image. As mentioned above, the merged classification map may include information contained in one or more of the plurality of classification maps. A merged classification map may only include information contained in one of the plurality of classification maps if, for example, the merged classification map is generated using information such as the tissue characterization confidence at each point and the selected classes with the highest degree of confidence are all from the same classification map.

Figure 14:
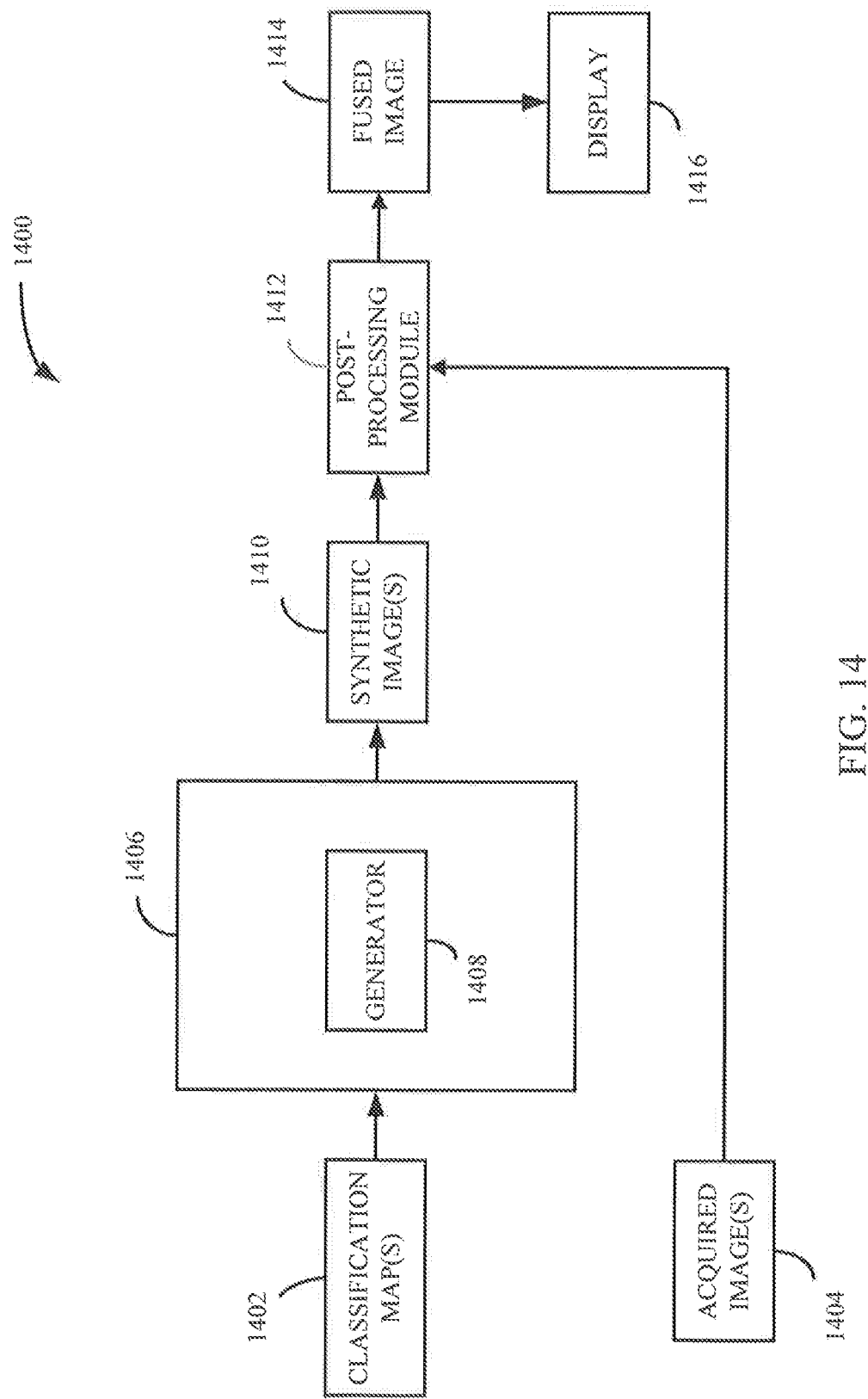
FIG. 14 is a block diagram of a system for fusing images of a subject in accordance with an embodiment.

In another embodiment, a system for generating images using a trained generative network (e.g., system 100 shown in FIG. 1) may be utilized to fuse a plurality of acquired images (e.g., a plurality of acquired images of the same physical segment acquired with different imaging modalities). FIG. 14 is a block diagram of a system for fusing images of a subject in accordance with an embodiment. In FIG. 14, the system 1400 includes a trained generative network 1406 and a post-processing module 1412. One or more classification maps 1402 each correspond to an acquired image of a physical segment acquired using a first imaging modality. The acquired images corresponding to the classification map(s) 1402 are to be fused with one or more acquired images 1404 of the same physical segment that are acquired with a second imaging modality that is different than the first imaging modality. The generative network 1406 may be used to covert the acquired images associated with the classification map(s) 1402 to the second imaging modality. The classification map(s) 1402 are input to the trained generative network 1406. As mentioned, the acquired image(s) corresponding to the classification map(s) 1402 are acquired with an imaging system associated with a first imaging modality, for example, an IVUS image acquired with an IVUS system. The classification map(s) may be generated, for example, using the method described above with respect to FIG. 3. In another embodiment, the classification map(s) 1402 may be derived from a source of data, such as a VH system integrated with an IVUS imaging system. The acquired images that correspond to the classification map(s) 1402 and the acquired images 1404 may be acquired with different imaging systems or may be acquired by a single hybrid system employing multiple imaging or classification technologies and outputting multiple sets of such data, where each set of data may be generated using a different technology of the hybrid system. The classification map(s) 1402 and the acquired image(s) 1404 may be retrieved, for example, from data storage (or memory) of an imaging system (e.g., an OCT system) or other computer system.

At least one classification map 1402 is provided as an input to the trained generative network 1406 such as, for example, generative network 104 shown in FIG. 1. The trained generative network 1406 (including generator 1408) generates one synthetic image 1410 associated with the second imaging modality based on each classification map 1402 (associated with the first imaging modality), i.e., the generative network 1406 converts the classification map 1402 from the first imaging modality to the second imaging modality. For example, the generator 1408 of generative network 1406 may receive a classification map 1402 associated with IVUS and generate a synthetic image 1410 associated with OCT. Each synthetic image 1410 generated for each classification map 1402 should be of the same modality (e.g., the second imaging modality) and should be the same modality (e.g., the second imaging modality) of any acquired image(s) 1404 to which the synthetic images will be fused using the post-processing module 1412. For example, the synthetic image(s) 1410 and the acquired images 1404 may be OCT images (e.g., intravascular OCT images). The post-processing module 1412 merges the plurality of synthetic images 1410 and the acquired images 1404 into a single fused image 1414. Before fusing the synthetic image(s) 1410 and the acquired images 1404, the post-processing module 1412 may be configured to align the synthetic image(s) 1410 and the acquired images 1404 using known methods for aligning images. In another embodiment, the acquired images used to generate the classification map(s) 1402 may be aligned with the acquired image(s) 1404 associated with the second imaging modality before the classification maps 1402 are generated. The post-processing module 1412 may use known methods to generate the fused image 1414 from the plurality of synthetic 1410 and acquired 1404 images. The single fused image 1414 generated by the post-processing module 1412 includes information contained in one or more of the images input to the post-processing module 1412. For example, the post-processing module 1412 may perform a pixel-wise weighted average of all input images (e.g., synthetic images 1410 and acquired images 1404), forming a superposition of the two or more images input to the post-processing module 1412. In another embodiment, no acquired image(s) 1404 are provided to the post-processing module 1412, and only the plurality of synthetic images 1410 are fused into a single fused image 1414 by the post-processing module 1412. The fused image 1414 may also be provided to and displayed on a display 1416. The fused image 1414 may be used by a user (e.g., a clinician) to guide diagnosis, prognosis, and decision making. A fused image 1414 may facilitate the interpretation of imaging data through consolidation of disparate datasets into a single coherent dataset. As mentioned above, the fused image may include information contained in one or more of the images input to the post-processing module. A fused image may only include information contained in one of the plurality of images input to the post-processing module if, for example, the fused image is generated using information such as the tissue characterization confidence of corresponding classification map(s) at each point and the selected classes with the highest degree of confidence are all from the same classification map.

Figure 15:
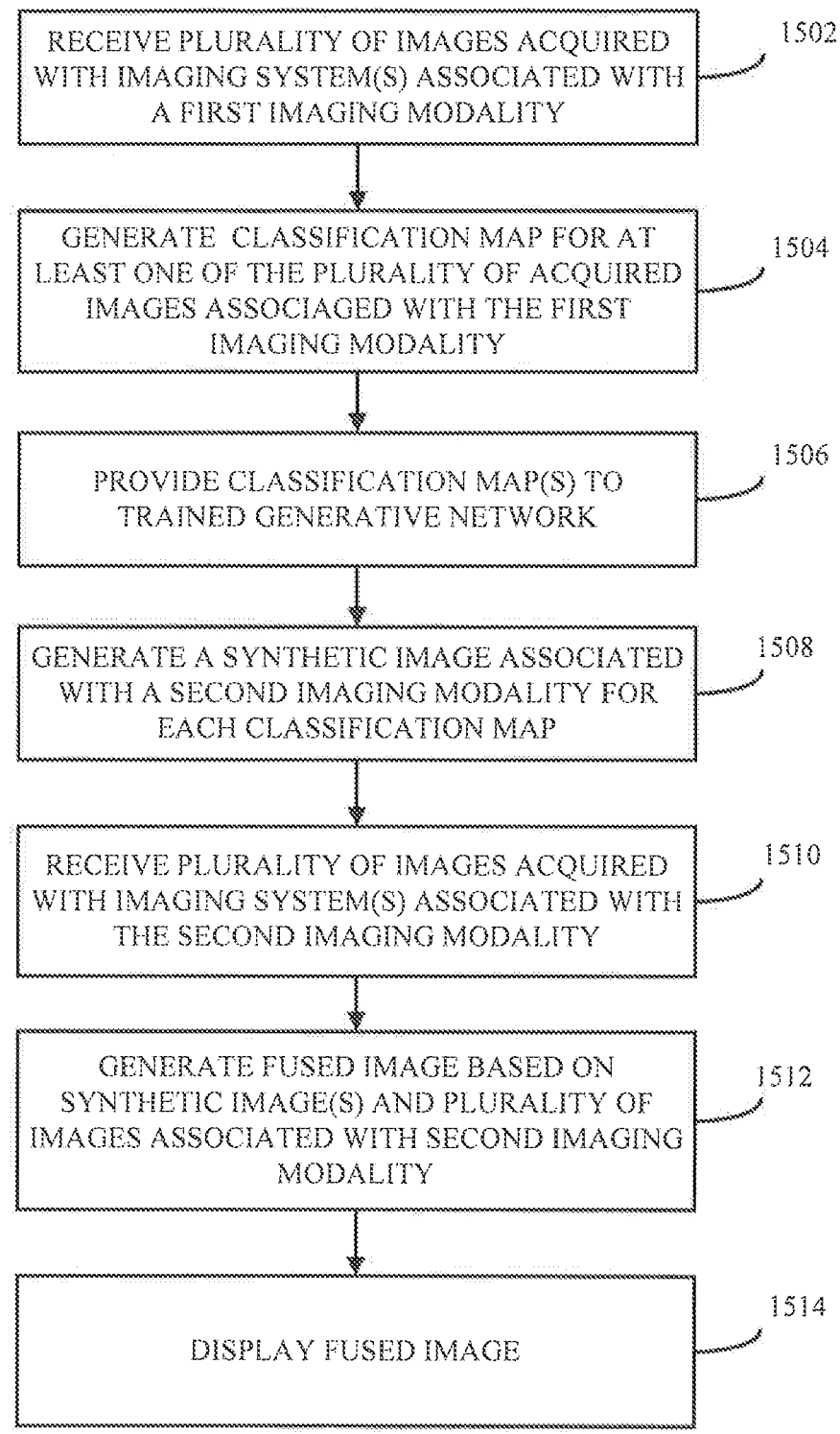
FIG. 15 illustrates a method for fusing images of subject in accordance with an embodiment.

FIG. 15 illustrates a method for fusing images of subject in accordance with an embodiment. At block 1502, a plurality of images of a physical segment acquired with an imaging system associated with a first imaging modality (e.g., IVUS) are received, for example, from one or more imaging systems or data storage. At block 1504, at least one classification map associated with the first imaging modality is generated based on the acquired images associated with the first imaging modality using, for example, the method described above with respect to FIG. 3. In another embodiment, one or more of the classification maps may be derived from a source of data such as VH based directly on radiofrequency analysis. At block 1506, each classification map is provided to a trained generative network (e.g., generative network 104 shown in FIG. 1). At block 1508, the trained generative network generates a synthetic image associated with a second imaging modality (e.g., OCT) based on each provided classification map. At block 1510, a plurality of images of the same physical segment acquired with an imaging system associated with the second imaging modality (e.g., OCT) are received, for example, from one or more imaging systems or data storage. At block 1512, the synthetic image(s) and acquired images associated with the second imaging modality may then be used to create or generate a single fused image by fusing the plurality of individual synthetic and acquired images associated with the second modality. Before fusing the synthetic image(s) and the acquired image(s), the synthetic image(s) and the acquired image(s) may be aligned using known methods for aligning images. In another embodiment, the acquired images used to generate the classification maps used to create the synthetic image(s) may be aligned with the acquired images associated with the second imaging modality before the classification maps are generated Known methods may be used to generate the fused image from the plurality of acquired or synthetic images associated with the second modality. For example, a pixel-wise weighted average of all input images may be performed, forming a superposition of the two or more input images. In another embodiment, no acquired image(s) may be included, and only a plurality of synthetic images are fused into a single fused image. The fused image may also be provided to and displayed on a display at block 1514. The fused image may be used by a user (e.g., a clinician) to guide diagnosis, prognosis, and decision making. A fused image may facilitate the interpretation of imaging data through consolidation of disparate datasets into a single coherent dataset.

Figure 16:
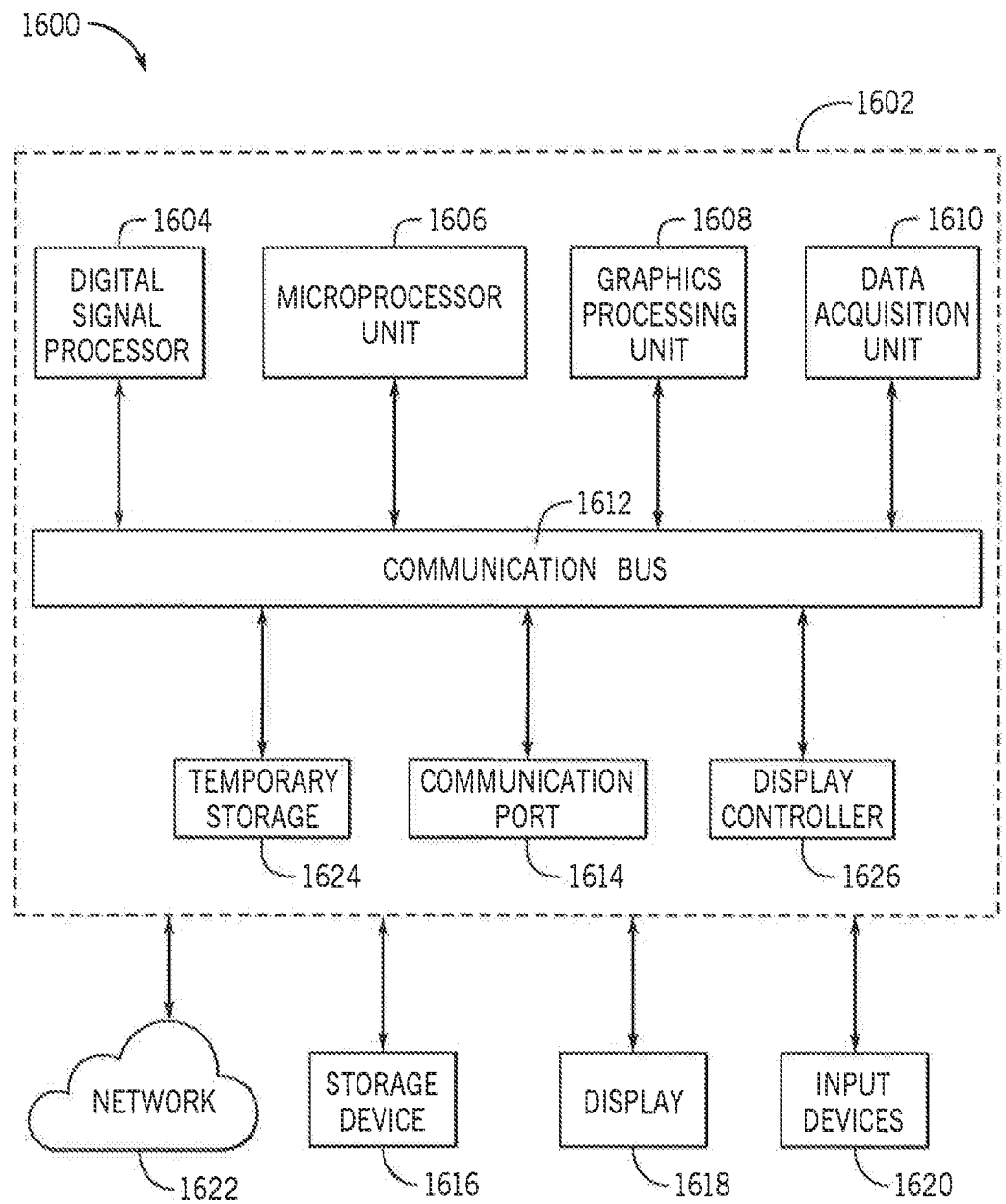
FIG. 16 is a block diagram of an example computer system in accordance with an embodiment.

FIG. 16 is a block diagram of an example computer system in accordance with an embodiment. Computer system 1600 may be used to implement the systems and methods described herein. In some embodiments, the computer system 1600 may be a workstation, a notebook computer, a tablet device, a mobile device, a multimedia device, a network server, a mainframe, one or more controllers, one or more microcontrollers, or any other general-purpose or application-specific computing device. The computer system 1600 may operate autonomously or semi-autonomously, or may read executable software instructions from the memory or storage device 1616 or a computer-readable medium (e.g., a hard drive, a CD-ROM, flash memory), or may receive instructions via the input device 1620 from a user, or any other source logically connected to a computer or device, such as another networked computer or server. Thus, in some embodiments, the computer system 1600 can also include any suitable device for reading computer-readable storage media.

Data, such as data acquired with an imaging system (e.g., an OCT imaging system, a CT imaging system, a magnetic resonance imaging (MM) system, etc.) may be provided to the computer system 1600 from a data storage device 1616, and these data are received in a processing unit 1602. In some embodiment, the processing unit 1602 includes one or more processors. For example, the processing unit 1602 may include one or more of a digital signal processor (DSP) 1604, a microprocessor unit (MPU) 1606, and a graphics processing unit (GPU) 1608. The processing unit 1602 also includes a data acquisition unit 1610 that is configured to electronically receive data to be processed. The DSP 1604, MPU 1606, GPU 1608, and data acquisition unit 1610 are all coupled to a communication bus 1612. The communication bus 1612 may be, for example, a group of wires, or a hardware used for switching data between the peripherals or between any component in the processing unit 1602.

The processing unit 1602 may also include a communication port 1614 in electronic communication with other devices, which may include a storage device 1616, a display 1618, and one or more input devices 1620. Examples of an input device 1620 include, but are not limited to, a keyboard, a mouse, and a touch screen through which a user can provide an input. The storage device 1616 may be configured to store data, which may include data such as classification maps and acquired images, whether these data are provided to, or processed by, the processing unit 1602. The display 1618 may be used to display images and other information, such as magnetic resonance images, patient health data, and so on.

The processing unit 1602 can also be in electronic communication with a network 1622 to transmit and receive data and other information. The communication port 1614 can also be coupled to the processing unit 1602 through a switched central resource, for example the communication bus 1612. The processing unit can also include temporary storage 1624 and a display controller 1626. The temporary storage 1624 is configured to store temporary information. For example, the temporary storage 1624 can be a random access memory.

Computer-executable instructions for generating synthetic medical images using a neural network and systems and methods for utilizing the synthetic images according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for completing a medical image having at least one obscured region, the system comprising:
   an input for receiving a first classification map generated using an acquired optical coherence tomography (OCT) image having at least one obscured region, the acquired OCT image acquired using an imaging system;
   a pre-processing module coupled to the input and configured to create an obscured region mask and to generate a second classification map that has the at least one obscured region filled in;
   a generative network coupled to the pre-processing module and configured to generate a synthetic OCT image based on the second classification map; and
   a post-processing module coupled to the generative network and configured to receive the synthetic OCT image and the acquired OCT image and to generate a completed image based on the synthetic OCT image and the acquired OCT image.

2. The system according to claim 1, further comprising a memory coupled to the post-processing module for storing the completed image.

3. The system according to claim 1, further comprising a display coupled to the post-processing module and configured to display the completed image.

4. The system according to claim 1, wherein the obscured region mask is created based on the classification map or the acquired OCT image.

5. The system according to claim 1, wherein the completed image is generated by replacing obscured pixels in the acquired OCT image with corresponding pixels in the synthetic OCT image.

6. The system according to claim 1, wherein the generative network is trained using a conditional generative adversarial network.

7. The system according to claim 1, wherein the classification map is generated by identifying a wall area of a vessel in the acquired OCT image and classifying at least one type of tissue in the wall area using a convolution neural network.

8. The system according to claim 7, wherein the at least one tissue type is one of calcium, lipid tissue, fibrous tissue, mixed tissue, non-pathological tissue or media, and no visible tissue.

9. The system according to claim 1, wherein the at least one obscured region is filled by determining the expected, likely or nominal classifications of a plurality of pixels in the obscured region.

10. A method for completing a medical image having at least one obscured region, the method comprising:
receiving a first classification map generated using an acquired optical coherence tomography (OCT) image having at least one obscured region, the acquired OCT image acquired using an imaging system;
creating an obscured region mask;
generating a second classification map that has the at least one obscured region filled in;
generating a synthetic OCT image based on the second classification map using a generative network;
generating a completed image based on the synthetic OCT image and the acquired OCT image; and
displaying the completed image on a display or storing the completed image in a memory.

11. The method according to claim 10, wherein the obscured region mask is created based on the classification map or the acquired OCT image.

12. The method according to claim 10, wherein generating the completed image includes replacing obscured pixels in the acquired OCT image with corresponding pixels in the synthetic OCT image.

13. The method according to claim 10, wherein the generative network is trained using a conditional generative adversarial network.

14. The method according to claim 10, wherein the first classification map is generated by identifying a wall area of a vessel in the acquired OCT image and classifying at least one type of tissue in the wall area using a convolution neural network.

15. The method according to claim 14, wherein the at least one tissue type is one of calcium, lipid tissue, fibrous tissue, mixed tissue, non-pathological tissue or media, and no visible tissue.

16. The method according to claim 10, wherein filling the obscured region mask of the classification map includes determining the expected, likely or nominal classifications of a plurality of pixels in the obscured region.

* * * * *